US009067906B2

(12) United States Patent
Kotani et al.

(10) Patent No.: US 9,067,906 B2
(45) Date of Patent: Jun. 30, 2015

(54) THERMOSETTING RESIN COMPOSITION, EPOXY RESIN MOLDING MATERIAL, AND POLYVALENT CARBOXYLIC ACID CONDENSATE

(71) Applicant: Hitachi Chemical Company, Ltd., Chiyoda-ku, Tokyo (JP)

(72) Inventors: Hayato Kotani, Tsukuba (JP); Naoyuki Urasaki, Tsukuba (JP); Makoto Mizutani, Tsukuba (JP)

(73) Assignee: Hitachi Chemical Company, Ltd., Tokyo (JP)

( * ) Notice: Subject to any disclaimer, the term of this patent is extended or adjusted under 35 U.S.C. 154(b) by 70 days.

(21) Appl. No.: 14/056,771

(22) Filed: Oct. 17, 2013

(65) Prior Publication Data

US 2014/0128621 A1 May 8, 2014

Related U.S. Application Data

(60) Division of application No. 12/805,445, filed on Jul. 30, 2010, now Pat. No. 8,637,593, which is a continuation-in-part of application No. 12/735,355, filed as application No. PCT/JP2009/050175 on Jan. 9, 2009, now Pat. No. 8,585,272.

(30) Foreign Application Priority Data

| Jan. 9, 2008 | (JP) | P2008-002128 |
| Jan. 11, 2008 | (JP) | P2008-004297 |
| Sep. 26, 2008 | (JP) | P2008-248711 |
| Oct. 2, 2008 | (JP) | P2008-257593 |

(51) Int. Cl.

| C08K 3/22 | (2006.01) |
| C08K 3/38 | (2006.01) |
| C08L 63/00 | (2006.01) |
| C08L 63/02 | (2006.01) |
| C08L 63/04 | (2006.01) |
| C07D 307/89 | (2006.01) |
| C08K 3/18 | (2006.01) |
| C08K 3/00 | (2006.01) |
| C08K 7/26 | (2006.01) |
| C08K 7/28 | (2006.01) |
| C08L 63/06 | (2006.01) |
| C07D 307/77 | (2006.01) |
| C08G 59/42 | (2006.01) |
| C08G 69/26 | (2006.01) |
| C08L 67/02 | (2006.01) |
| H01L 33/56 | (2010.01) |

(52) U.S. Cl.
CPC ............... *C07D 307/89* (2013.01); *C08K 3/18* (2013.01); *C08K 3/0033* (2013.01); *C08K 3/38* (2013.01); *C08K 2003/222* (2013.01); *C08K 2003/2227* (2013.01); *C08K 2003/2241* (2013.01); *C08K 3/2279* (2013.01); *C08K 7/26* (2013.01); *C08K 7/28* (2013.01); *C08L 63/04* (2013.01); *C08L 63/06* (2013.01); *C07D 307/77* (2013.01); *C08G 59/4246* (2013.01); *C08G 69/26* (2013.01); *C08L 63/00* (2013.01); *C08L 67/02* (2013.01); *H01L 33/56* (2013.01)

(58) Field of Classification Search
None
See application file for complete search history.

(56) References Cited

U.S. PATENT DOCUMENTS

| 3,388,185 | A | 6/1968 | Goldberg et al. |
| 5,428,082 | A | 6/1995 | Gould et al. |
| 2004/0092668 | A1 | 5/2004 | Kawaguchi et al. |
| 2009/0315049 | A1 | 12/2009 | Urasaki et al. |
| 2011/0031527 | A1 | 2/2011 | Kotani et al. |

FOREIGN PATENT DOCUMENTS

| CN | 1357929 A | 7/2002 |
| CN | 1965012 A | 5/2007 |
| CN | 101037529 A | 9/2007 |
| CN | 101072808 A | 11/2007 |
| EP | 1 754 734 A1 | 2/2007 |
| EP | 2 100 908 A1 | 9/2009 |
| JP | S48-3716 | 2/1973 |
| JP | S52-108496 | 9/1977 |
| JP | S54-023014 | 8/1979 |
| JP | 55-110117 | 8/1980 |
| JP | 58-025325 | 2/1983 |
| JP | 58-25325 A | 2/1983 |
| JP | H6-136090 | 5/1994 |
| JP | 07-292073 | 11/1995 |
| JP | 08-193122 | 7/1996 |
| JP | 63-258924 | 10/1998 |
| JP | 11-279449 | 10/1999 |
| JP | 11-279449 A | 10/1999 |

(Continued)

OTHER PUBLICATIONS

International Search Report for PCT/JP2009/050175 mailed Aug. 19, 2010.
Search Report issued Nov. 1, 2011, in the corresponding Application No. PCT/JP2011/067365 (9 pages).
Notification of Information Provision, issued from the Commissioner of the Japanese Patent Office, in related Japanese Patent Application No. P2010-158083, mailed Mar. 21, 2012.
Notification of Information Provision, issued from the Commissioner of the Japanese Patent Office, in related Japanese Patent Application No. 2010-105524, mailed Mar. 21, 2012.

(Continued)

*Primary Examiner* — Robert Sellers
(74) *Attorney, Agent, or Firm* — Fitch Even Tabin & Flannery LLP

(57) ABSTRACT

The epoxy resin molding material of the invention comprises (A) an epoxy resin and (B) a curing agent, wherein the (B) curing agent contains a polyvalent carboxylic acid condensate. The thermosetting resin composition of the invention comprises (A) an epoxy resin and (B) a curing agent, wherein the viscosity of the (B) curing agent is 1.0-1000 mPa·s at 150° C., as measured with an ICI cone-plate Brookfield viscometer.

2 Claims, 9 Drawing Sheets

(56) References Cited

FOREIGN PATENT DOCUMENTS

| JP | 11-302507 | 11/1999 |
|---|---|---|
| JP | 2000-001632 | 1/2000 |
| JP | 2003-160640 | 6/2003 |
| JP | 2005-0362182 | 2/2005 |
| JP | 2006-140207 | 6/2006 |
| JP | 2006-140207 A | 6/2006 |
| JP | 2007-297601 | 11/2007 |
| JP | 2010-100798 | 5/2010 |
| TW | 200938560 A | 9/2009 |
| WO | WO 2005/121202 | 12/2005 |
| WO | WO 2006/043608 | 4/2006 |
| WO | 2006/121090 A1 | 11/2006 |
| WO | WO 2007/142018 | 12/2007 |
| WO | WO 2009-088059 A1 | 7/2009 |

OTHER PUBLICATIONS

Office Action, from the Taiwan Patent Office, issued in the counterpart Taiwan Patent Application No. 098100613, dated Sep. 25, 2012, 11 pages in Chinese, and 1 page in its partial English translation.

Office Action from the Chinese Patent Office issued in the counterpart Chinese Patent Application No. 200980101801.4, dated Nov. 16, 2012, 6 pages In Chinese, and 1 page in its partial English translation.

Notification of Transmittal of Translation of the International Preliminary Report on Patentability and the Written Opinion of the International Searching Authority issued from the International Bureau in the counterpart International Application No. PCT/JP2011/067365, mailed Feb. 14, 2013.

Office Action from US Patent Office for corresponding U.S. Patent Publication 2011-0031527, mailed Mar. 29, 2013, 9 pages.

Hayato G. et al., "Thermosetting-resin composition for forming cured material used for manufacturing substrate for optical-semiconductor element mounting, comprises epoxy resin, and hardening agent with viscosity of present range at present temperature", Derwent accession No. 2009-L52409 for PCT Publication No. WO2009/088059A1, Jul. 16, 2009, 5 pages.

Office Action from Japanese Patent Office for corresponding Japanese Patent Application 2010-085392, mailed Jun. 11, 2013.

European Search Report from European Patent Office issued in counterpart European Application No. 13165927.8-1302, dated Jul. 25, 2013, pp. 1-7.

Office action issued by the State Intellectual Property Office of the People's Republic of China on Aug. 14, 2014, in regards to counterpart Chinese Patent Application No. 201180033517.5.

Office action issued by the State Intellectual Property Office of the People's Republic of China on Aug. 21, 2014, in regards to counterpart Chinese Patent Application No. 20120154424.4.

Tao Zhang, et al., "Degradation and drug delivery properties of poly (1,4-cyclohexanedicarboxylic anhydride)", Journal of Biomaterials Science-Polymer Edition vol. 12 No. 5, Dec. 31, 2001, p. 491-p. 501.

Office Action from Republic of China, Taiwan Patent Office in a corresponding patent application No. 100127018 dated Dec. 11, 2013, 7 pages in Chinese.

Office Action in Counterpart Application CN 201210444060.3, dated Dec. 18, 2014 (6 pgs.).

Office Action from State Intellectual Property Office of People's Republic of China in the corresponding Patent Application No. 201210444060.3 dated Mar. 25, 2014, 7 pages in Chinese.

(a)

(b)

(c)

(a)

(b)

THERMOSETTING RESIN COMPOSITION, EPOXY RESIN MOLDING MATERIAL, AND POLYVALENT CARBOXYLIC ACID CONDENSATE

CROSS-REFERENCE TO RELATED APPLICATIONS

This is a Divisional of prior U.S. application Ser. No. 12/805,445 filed on Jul. 30, 2010, U.S. Pat. No. 8,637,593, which is a Continuation-In-Part application of prior U.S. application Ser. No. 12/735,355 filed on Jul. 8, 2010, U.S. Pat. No. 8,585,272, which is prior application PCT/JP2009/050175 filed on Jan. 9, 2009.

INCORPORATION BY REFERENCE

U.S. application Ser. No. 12/735,355 filed on Jul. 8, 2010, is incorporated by reference herein in its entirety. PCT/JP2009/050175 filed on Jan. 9, 2009, is incorporated by reference herein in its entirety. Japanese Patent application 2008-257593 filed Oct. 2, 2008 is incorporated herein in its entirety. Japanese Patent application 2008-248711 filed Sep. 26, 2008 is incorporated herein in its entirety. Japanese Patent application 2008-004297 filed Jan. 11, 2008 is incorporated herein in its entirety. Japanese Patent application 2008-002128 filed Jan. 9, 2008 is incorporated herein in its entirety.

TECHNICAL FIELD

The present invention relates to a thermosetting resin composition, an epoxy resin molding material, a photosemiconductor element mounting board and a method for producing it, and a photosemiconductor device. The invention further relates to a polyvalent carboxylic acid condensate, and an epoxy resin curing agent, an epoxy resin composition, a polyamide resin and a polyester resin, which employ the same.

BACKGROUND ART

Photosemiconductor devices incorporating photosemiconductor elements such as LEDs (Light Emitting Diodes) and fluorescent materials have high energy efficiency and long life spans, and are therefore used in outdoor displays, portable liquid crystal backlights, vehicle devices and the like, with ever increasing demand. With the advances in high luminance of LED devices, it has become a goal to prevent deterioration of photosemiconductor devices due to increased junction temperature caused by increased element heat generation or by increased direct light energy.

Patent document 1 discloses a photosemiconductor element mounting board employing a thermosetting resin composition that comprises an epoxy resin and a curing agent such as an acid anhydride.

Acid anhydrides are commonly used as curing agents for epoxy resins. They are also used as starting materials to obtain polyimide compounds by reaction with diamines. Acid anhydrides are inexpensive and superior from the standpoint of transparency, electrical insulating properties, chemical resistance, humidity resistance and adhesion. Acid anhydrides are therefore used for a variety of purposes including electrical insulating materials, semiconductor device materials, photosemiconductor sealing materials, adhesive materials and coating materials.

One class of acid anhydrides is that of polycarboxylic anhydrides formed by polycondensation of polyvalent carboxylic acids. For example, polycarboxylic anhydrides obtained by dehydrating condensation reaction between aliphatic dicarboxylic acid molecules such as polyazelaic acid or polysebacic acid are sometimes used as curing agents or curing accelerators for thermosetting resins such as epoxy resins, melamine resins and acrylic powder coatings. The polycarboxylic anhydrides obtained by dehydrating condensation reaction between aliphatic dicarboxylic acid molecules are useful as curing agents for powder coatings or casting resins because they readily yield cured products exhibiting excellent flexibility and thermal shock resistance.

Incidentally, other uses of acid anhydrides include biomedical applications as proposed in Patent document 2, which employs a high molecular weight polycarboxylic anhydride (polyvalent carboxylic acid condensate) with an average molecular weight exceeding 20000, obtained by condensation between aliphatic and aromatic dicarboxylic acid molecules.

[Patent document 1] JP 2006-140207 A
[Patent document 2] JP 63-258924 A

DISCLOSURE OF THE INVENTION

Problems to be Solved by the Invention

However, acid anhydride curing agents employed as curing agents for thermosetting resins such as epoxy resins are not as abundantly available as polyamine, phenol-novolac and imidazole-based curing agents. The polycarboxylic anhydrides do not have molecular designs suitable as curing agents for epoxy resins, and their uses are therefore limited.

Conventional polycarboxylic anhydrides used as curing agents for epoxy resins are advantageous compared to ordinary acid anhydride-based curing agents, from the viewpoint of cured flexibility and thermal shock resistance, but it has been difficult to form transparent cured products with low coloration using them.

It has been attempted to introduce alicyclic structures into acid anhydride-based curing agents with an aim toward their application in optical materials with excellent ultraviolet resistance, heat coloration resistance and optical characteristics. However, conventional alicyclic acid anhydrides generally have low melting points of below 40° C., and therefore their uses have been limited. On the other hand, most aromatic or linear or cyclic aliphatic tetracarboxylic anhydrides conventionally used in combination with diamines to form polyimide resins have melting points of 150° C. and higher, and they have not been easily suitable for applications other than polyimide resin starting materials.

When it is attempted to produce a photosemiconductor mounting board by transfer molding with a conventional thermosetting resin composition, the resin composition exudes through the gap between the cope and drag of the die during molding, tending to result in resin smudge. When resin smudge occurs during hot molding, the resin smudge spreads out to the openings (recesses) in the board serving as the photosemiconductor element-mounted region, causing interference to photosemiconductor element mounting. Even when a photosemiconductor element has been successfully mounted on an opening, the resin smudge can sometimes create problems such as connection defects during electrical connection between the photosemiconductor element and metal wiring by bonding wires. Therefore, resin smudge at the openings of a board requires addition of a resin smudge removal step in the production process for photosemiconductor element mounting boards. Since such removal steps are associated with lower workability and increased production time loss and production cost, it is desirable to minimize resin smudge.

It is an object of the present invention, which has been accomplished in light of these circumstances, to provide a thermosetting resin composition and epoxy resin molding material with reduced resin smudge during molding and sufficiently excellent moldability, as well as a photosemiconductor element mounting board and method for producing the same, and a photosemiconductor device, which employ the same.

It is another object of the invention to provide a polyvalent carboxylic acid condensate that can yield transparent cured products with low coloration when used as an epoxy resin curing agent.

Means for Solving the Problems

The invention provides an epoxy resin molding material comprising (A) an epoxy resin and (B) a curing agent, wherein the (B) curing agent contains a polyvalent carboxylic acid condensate.

The invention further provides a thermosetting resin composition comprising (A) an epoxy resin and (B) a curing agent, wherein the viscosity of the (B) curing agent is 1.0-1000 mPa·s at 150° C., as measured with an ICI cone-plate Brookfield viscometer.

The invention still further provides a thermosetting resin composition comprising (A) an epoxy resin and (B) a curing agent, wherein the (B) curing agent contains a polyvalent carboxylic acid condensate with a component represented by the following formula (1). In formula (1), $R_x$ represents a divalent organic group, multiple $R_x$ groups in the same molecule can be the same or different, $R_y$ represents a monovalent organic group and the two $R_y$ groups in the same molecule can be the same or different, and $n^1$ represents an integer of 1 or greater.

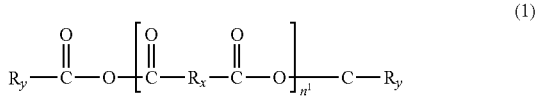

(1)

The (B) curing agent containing a polyvalent carboxylic acid condensate comprising this component, when used as a transfer molding material, for example, can easily exhibit a melting point and viscosity suitable for requirements in terms of flow property, moldability, workability, storage stability and freedom of composition design. A thermosetting resin composition of the invention having such a structure therefore has reduced resin smudge during molding and exhibits sufficiently excellent moldability.

$R_x$ is a divalent group with an aliphatic hydrocarbon ring, wherein the aliphatic hydrocarbon ring is optionally substituted with a halogen atom or a straight-chain or branched hydrocarbon group, and $R_y$ is preferably a monovalent hydrocarbon group optionally substituted with an acid anhydride or carboxylic acid ester group.

$R_x$ is preferably a divalent group represented by the following formula (10). In formula (10), m represents an integer of 0-4, $R_z$ represents a halogen atom or straight-chain or branched C1-4 hydrocarbon group, and when m is 2-4 the multiple $R_z$ groups can be the same or different and linked together to form a ring.

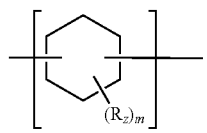

(10)

$R_y$ is preferably a monovalent group represented by the following chemical formula (20), or a monovalent group derived by removing a hydrogen from a cyclic aliphatic hydrocarbon selected from among cyclobutane, cyclopentane, cyclohexane, cycloheptane, cyclooctane, norbornane, dicyclopentadiene, adamantane, naphthalene hydride and biphenyl hydride.

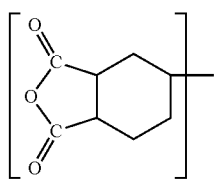

(20)

From the viewpoint of inhibiting coloration of the thermosetting resin composition, the component represented by formula (1) above preferably includes a component represented by the following formula (1a).

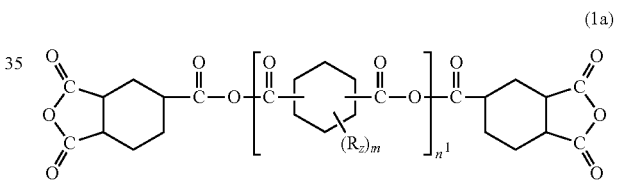

(1a)

The number-average molecular weight of the polyvalent carboxylic acid condensate is preferably 300-20000. The viscosity of the polyvalent carboxylic acid condensate as measured with an ICI cone-plate Brookfield viscometer is preferably 10-30000 mPa·s at 150° C.

The (B) curing agent in the thermosetting resin composition of the invention can further contain an acid anhydride formed by ring-closing condensation of a polyvalent carboxylic acid in the molecule. The (B) curing agent preferably further includes a polyvalent carboxylic acid condensate represented by the following chemical formula (3).

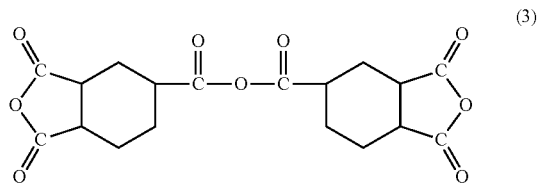 [SMILES: O=C(OC(=O)C1CCC2C(=O)OC(=O)C2C1)C1CCC2C(=O)OC(=O)C2C1]

(3)

The content of the (B) curing agent in the thermosetting resin composition of the invention is preferably 10-150 parts by weight with respect to 100 parts by weight of the (A) epoxy resin. The equivalent ratio of epoxy groups in the (A) epoxy resin and acid anhydride groups in the (B) curing agent that are reactive with epoxy groups is preferably between 1:0.3 and 1:1.2. This can further minimize resin smudge during molding of the thermosetting resin composition of the invention.

The thermosetting resin composition of the invention preferably further comprises (D) a white pigment to increase the optical reflectance from the visible light to the near ultraviolet light range after curing.

The (D) white pigment preferably includes at least one inorganic material selected from the group consisting of alumina, magnesium oxide, antimony oxide, titanium oxide, zirconium oxide and inorganic hollow particles.

From the viewpoint of improving dispersibility in the thermosetting resin composition, the center particle size of the (D) white pigment is preferably 0.1-50 μm.

A (D) white pigment content of 10-85 vol % with respect to the total thermosetting resin composition will give the thermosetting resin composition of the invention more excellent moldability.

The invention further provides a photosemiconductor element mounting board having a recess composed of the bottom face and the wall faces, wherein the bottom face of the recess is the photosemiconductor element mounting section and at least parts of the wall faces of the recess are made of a cured thermosetting resin composition or epoxy resin molding material of the invention.

The invention still further provides a method for producing a photosemiconductor element mounting board having a recess composed of the bottom face and the wall faces, the method for producing a photosemiconductor element mounting board comprising a step of forming at least parts of the wall faces of the recess using a thermosetting resin composition or cured epoxy resin molding material of the invention.

The invention still further provides a photosemiconductor device comprising a photosemiconductor element mounting board having a recess composed of the bottom face and the wall faces, a photosemiconductor element disposed in the recess of the photosemiconductor element mounting board and a sealing resin section in which the recess is filled to seal the photosemiconductor element, wherein at least parts of the wall faces of the recess are made of a cured thermosetting resin composition or epoxy resin molding material of the invention.

The invention further relates to a polyvalent carboxylic acid condensate comprising a component represented by the following formula (I). In formula (I), $R_x$ represents a divalent group with an aliphatic hydrocarbon ring, wherein the aliphatic hydrocarbon ring is optionally substituted with a halogen atom or a straight-chain or branched hydrocarbon group, and multiple $R_x$ groups in the same molecule can be the same or different. $R_y$ represents a monovalent hydrocarbon group optionally substituted with an acid anhydride or carboxylic acid ester group, and the two $R_y$ groups in the same molecule can be the same or different. The symbol $n^1$ represents an integer of 1 or greater.

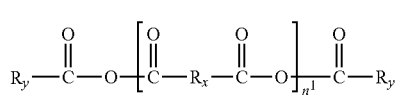

When the polyvalent carboxylic anhydride of the invention is used as an epoxy resin curing agent, it can yield transparent cured products with minimal coloration.

In formula (I), $R_x$ is preferably a divalent group derived by removing a hydrogen from a cyclic aliphatic hydrocarbon selected from among cyclobutane, cyclopentane, cyclohexane, cycloheptane, cyclooctane, norbornane, dicyclopentadiene, adamantane, naphthalene hydride and biphenyl hydride. The cyclic aliphatic hydrocarbon can be optionally substituted with a halogen atom or a straight-chain or branched hydrocarbon group.

Also in formula (I), $R_x$ is preferably a divalent group represented by formula (10) above.

Also in formula (I), $R_y$ is preferably a monovalent group represented by chemical formula (20) above, or a monovalent group derived by removing a hydrogen from a cyclic aliphatic hydrocarbon selected from among cyclobutane, cyclopentane, cyclohexane, cycloheptane, cyclooctane, norbornane, dicyclopentadiene, adamantane, naphthalene hydride and biphenyl hydride.

The polyvalent carboxylic acid condensate of the invention can include a component represented by formula (Ia) above.

The polyvalent carboxylic acid condensate can further include a component represented by the following formula (2). In formula (2), $R_x$ has the same definition as $R_x$ in formula (I), including its preferred examples. The symbol $n^2$ represents an integer of 2 or greater.

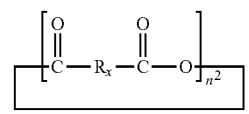

The polyvalent carboxylic acid condensate of the invention can be obtained by a method comprising a step of intermolecular dehydrating condensation between carboxyl groups of a reaction mixture containing a polyvalent carboxylic acid represented by the following formula (5) and a monocarboxylic acid represented by the following formula (6). In formulas (5) and (6), $R_x$ and $R_y$ have the same definitions as $R_x$ and $R_y$ in formula (I), including their preferred examples.

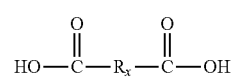

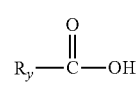

In formulas (I) and (1a), $n^1$ is preferably an integer of 1-200.

The number-average molecular weight Mn of the polyvalent carboxylic acid condensate of the invention is preferably 300-20000. The viscosity of the polyvalent carboxylic acid condensate as measured with an ICI cone-plate Brookfield viscometer is preferably 10-30000 mPa·s at 150° C.

The method for producing a polyvalent carboxylic acid according to the invention comprises a step of intermolecular dehydrating condensation between carboxyl groups in a reaction mixture containing a polyvalent carboxylic acid represented by formula (5) above and a monocarboxylic acid represented by formula (6) above.

The reaction mixture preferably further contains a compound selected from among acetic anhydride, propionic anhydride, acetyl chloride, fatty acid chlorides and organic bases.

The epoxy resin curing agent of the invention comprises a polyvalent carboxylic acid condensate according to the invention. An epoxy resin curing agent of the invention can yield a transparent cured product with minimal coloration.

In addition to the polyvalent carboxylic acid condensate, the epoxy resin curing agent of the invention can further comprise an acid anhydride compound that can be obtained by intramolecular dehydrating condensation between carboxyl groups.

The method for producing an epoxy resin curing agent according to the invention comprises a step of melt mixing a polyvalent carboxylic acid condensate of the invention and an acid anhydride compound that can be obtained by intramolecular dehydrating condensation between the carboxyl groups of a polyvalent carboxylic acid.

The epoxy resin composition of the invention includes an epoxy resin with two or more epoxy groups, and an epoxy resin curing agent according to the invention. The epoxy resin composition of the invention can yield a transparent cured product with minimal coloration.

The epoxy resin is preferably an alicyclic epoxy resin having a saturated hydrocarbon group derived by removing a hydrogen atom from a cyclic aliphatic hydrocarbon selected from among cyclobutane, cyclopentane, cyclohexane, cycloheptane, cyclooctane, norbornane, dicyclopentadiene, adamantane, naphthalene hydride and biphenyl hydride, wherein the cyclic saturated hydrocarbon is optionally substituted with a halogen atom or straight-chain or branched hydrocarbon group.

The cured product of the invention is obtained by thermal curing the aforementioned epoxy resin composition. The cured product is preferably transparent.

The invention further relates to a polyamide resin obtainable by polycondensation between a polyvalent carboxylic acid condensate of the invention as described above, and a polyamine with two or more amino groups. The polyamide resin of the invention has superior transparency compared to conventional polyamide resins. Also, using an acid anhydride provides higher reactivity than a conventional dicarboxylic acid and polyamine reaction, and allows reaction at low temperature and in a shorter period of time, and therefore the polyamide resin of the invention is also superior in terms of productivity.

The invention further relates to a polyester resin obtainable by polycondensation between a polyvalent carboxylic acid condensate of the invention as described above, and a polyalcohol with two or more hydroxyl groups. The polyester resin of the invention has superior transparency compared to conventional polyester resins. Also, using an acid anhydride provides higher reactivity than a conventional dicarboxylic acid and polyalcohol reaction, and allows reaction at low temperature and in a shorter period of time, and therefore the polyester resin of the invention is also superior in terms of productivity.

Effect of the Invention

According to the invention it is possible to provide a thermosetting resin composition and epoxy resin molding material with reduced resin smudge during molding and sufficiently excellent moldability, as well as a photosemiconductor element mounting board and method for producing the same, and a photosemiconductor device, which employ the same.

When used as a curing agent for thermosetting resins such as epoxy resins, the polyvalent carboxylic acid condensate of the invention can yield transparent cured products with low coloration. The polyvalent carboxylic acid condensate of the invention provides a novel alternative for acid anhydride curing agents, for which fewer types have been available compared to polyamine, phenol-novolac and imidazole-based curing agents.

Although conventional alicyclic acid anhydrides have been used as curing agents for liquid epoxy resin compositions employed in photosemiconductor sealing materials, adhesive materials, coating material materials and the like, the melting temperatures are generally low at below 40° C., which has limited their use. In contrast, the epoxy resin curing agent of the invention, when used as a transfer molding material, for example, allows a suitable melting point and viscosity to be easily obtained for requirements in terms of flow property, moldability, workability, storage stability and freedom of composition design.

According to the invention, it is possible to obtain a polyvalent carboxylic acid condensate with a low melting point. Most aromatic or straight-chain or cyclic aliphatic tetracarboxylic anhydrides conventionally used in combination with diamines to form polyimide resins have melting points of 150° C. and higher, and they have not been easily suitable for applications other than polyimide resin starting materials. The polyvalent carboxylic acid of the invention is also advantageous in terms of cost, because it can be utilized for a wider range of purposes.

EXPLANATION OF SYMBOLS

Figure 1:
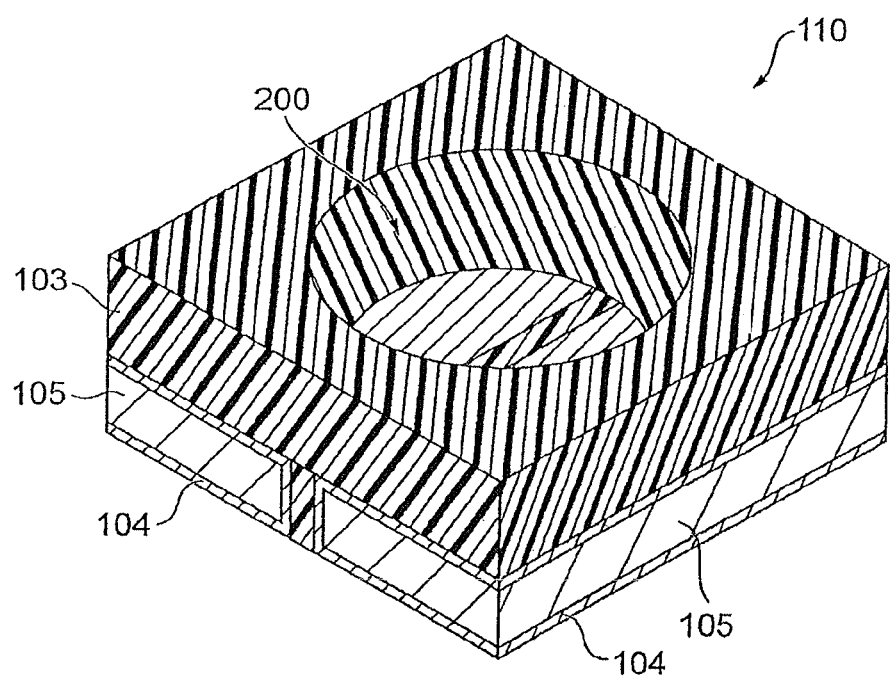
FIG. 1 is a perspective view showing an embodiment of a photosemiconductor element mounting board of the invention.

100: Photosemiconductor element, 101: transparent sealing resin, 102: bonding wire, 103: cured thermosetting resin composition (reflector), 104: Ni/Ag plating, 105: metal wiring, 106: fluorescent material, 107: solder bump, 110: photosemiconductor element mounting board, 200: photosemiconductor element mounting region, 150: resin sprue, 151: die, 300: LED element, 301: bonding wire, 302: transparent sealing resin, 303: reflector, 304: lead, 305: fluorescent material, 306: die bond material, 400: burr-measuring die (cope), 401: burr-measuring die (drag), 402: resin sprue, 403: cavity, 404:

slit (75 μm), 405: slit (50 μm), 406: slit (30 μm), 407: slit (20 μm), 408: slit (10 μm), 409: slit (2 μm), 410: resin burrs.

BEST MODES FOR CARRYING OUT THE INVENTION

Preferred embodiments of the invention will now be explained in detail, with reference to the accompanying drawings as necessary. Throughout the drawings, corresponding elements will be referred to by like reference numerals and will be explained only once. Unless otherwise specified, the vertical and horizontal positional relationships are based on the positional relationships in the drawings. Also, the dimensional proportions depicted in the drawings are not necessarily limitative. The term "(meth)acrylate" used throughout the present specification refers to the "acrylate" and its corresponding "methacrylate".

[Thermosetting Resin Composition]

The thermosetting resin composition according to one embodiment of the invention is a thermosetting resin composition comprising (A) an epoxy resin and (B) a curing agent, wherein the viscosity of the (B) curing agent is 1.0-1000 mPa·s at 150° C., as measured with an ICI cone-plate Brookfield viscometer.

The thermosetting resin composition according to another embodiment of the invention comprises (A) an epoxy resin and (B) a curing agent, wherein the (B) curing agent contains a polyvalent carboxylic acid condensate with a component represented by formula (1) above.

<(A) Epoxy Resin>

The (A) epoxy resin can be one commonly used in epoxy resin molding materials for sealing of electronic parts. As examples of epoxy resins there can be mentioned epoxidated novolac resins of phenols and aldehydes such as phenol-novolac-type epoxy resins and orthocresol-novolac-type epoxy resins, diglycidyl ethers of bisphenol A, bisphenol F, bisphenol S and alkyl-substituted bisphenols, glycidylamine-type epoxy resins obtained by reaction of epichlorohydrin with polyamines such as diaminodiphenylmethane and isocyanuric acid, linear aliphatic epoxy resins obtained by oxidation of olefin bonds with peracids such as peracetic acid, and alicyclic epoxy resins. Any of these can be used alone or in combinations of two or more.

Preferred of these are bisphenol A-type epoxy resins, bisphenol F-type epoxy resins, bisphenol S-type epoxy resins, diglycidyl isocyanurate, triglycidyl isocyanurate, and diglycidyl dicarboxylate esters derived from 1,2-cyclohexanedicarboxylic acid, 1,3-cyclohexanedicarboxylic acid or 1,4-cyclohexanedicarboxylic acid, because of their relatively low coloration. For the same reason, diglycidyl esters of dicarboxylic acids such as phthalic acid, tetrahydrophthalic acid, hexahydrophthalic acid, methyltetrahydrophthalic acid, nadic acid and methylnadic acid are preferred. There can also be mentioned glycidyl esters of nucleus-hydrogenated trimellitic acid and nucleus-hydrogenated pyromellitic acid having an alicyclic structure with hydrogenated aromatic rings. There can further be mentioned polyorganosiloxanes with epoxy groups, produced by heating a silane compound in the presence of an organic solvent, an organic base and water for hydrolysis and condensation. As component (A) there can be used an epoxy resin represented by the following formula (7), which is a copolymer of a glycidyl (meth)acrylate monomer and a monomer that is polymerizable therewith.

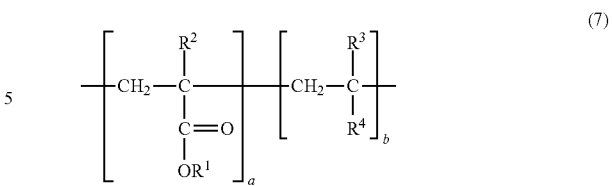

In formula (7), $R^1$ represents a glycidyl group, $R^2$ and $R^3$ each independently represent hydrogen or a C1-6 saturated or unsaturated monovalent hydrocarbon group, and $R^4$ represents a monovalent saturated hydrocarbon group. The letters a and b represent positive integers.

In order to inhibit coloration of cured products, the epoxy resin is preferably an alicyclic epoxy resin having an aliphatic hydrocarbon group derived by removing a hydrogen atom from a cyclic aliphatic hydrocarbon selected from among cyclobutane, cyclopentane, cyclohexane, cycloheptane, cyclooctane, norbornane, dicyclopentadiene, adamantane, naphthalene hydride and biphenyl hydride. The cyclic aliphatic hydrocarbon can be optionally substituted with a halogen atom or a straight-chain or branched hydrocarbon group.

<(B) Curing Agent>

The curing agent of this embodiment can contain a polyvalent carboxylic acid condensate, and the viscosity of the (B) curing agent is preferably 1.0-1000 mPa·s and more preferably 10-200 mPa·s at 150° C., as measured with an ICI cone-plate Brookfield viscometer. If the viscosity of the (B) curing agent is within this specified range, satisfactory moldability, with minimal burr generation, will be obtained when the polyvalent carboxylic acid condensate-containing thermosetting resin composition is used for transfer molding, for example. The method for adjusting the viscosity of the curing agent can be a method of adjusting the viscosity of the polyvalent carboxylic acid condensate by controlling the average molecular weight of the polyvalent carboxylic acid condensate, or a method of modifying the mixing ratio of the polyvalent carboxylic acid condensate and a curing agent that is compatible therewith.

The viscosity of a polyvalent carboxylic acid condensate suitable for adjusting the viscosity of the (B) curing agent is preferably 10-30000 mPa·s and more preferably 10-10000 mPa·s at 150° C. If the viscosity of the polyvalent carboxylic acid condensate is less than 10 mPa·s in this temperature range, the effect of inhibiting resin smudge during transfer molding can be lowered, while if it is greater than 30000 mPa·s the flow property of the thermosetting resin composition can be reduced in the die during transfer molding. The viscosity of the polyvalent carboxylic acid condensate can be measured using an ICI cone-plate Brookfield viscometer by Research Equipment (London) Ltd., for example.

The term "polyvalent carboxylic acid condensate" used throughout the present specification means a polymer formed by condensation between the molecules of one or more polyvalent carboxylic acids with two or more carboxyl groups. More specifically, the polyvalent carboxylic acid condensate is a polymer wherein the carboxy groups between the molecules of a monomer with 2 or more molecules having 2 or more carboxyl groups undergo dehydrating condensation to produce acid anhydride groups (acid anhydride bonds), and each monomer unit is linked in a chain or cyclic fashion by the produced acid anhydride groups. The term "acid anhydride compound obtainable by intramolecular dehydrating condensation between the carboxyl groups of a polyvalent carboxylic acid" means an acid anhydride compound having a cyclic structure containing acid anhydride groups, the acid anhydride groups being produced by intramolecular dehydrating condensation between the carboxyl groups of a polyvalent carboxylic acid having 2 or more carboxyl groups.

The polyvalent carboxylic acid condensate of this embodiment will usually be composed of a plurality of components with different polymerization degrees, and it can contain a plurality of components with different repeating units and end groups. The polyvalent carboxylic acid condensate of this embodiment also preferably contains a component represented by the following formula (1) as a major component. In formula (1), $R_x$ represents a divalent organic group and $R_y$ represents a monovalent organic group. The proportion of the component of formula (1) is at least 60 wt % based on the total weight of the polyvalent carboxylic acid condensate.

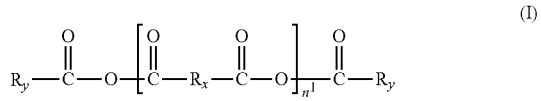

(1)

In formula (1), $R_x$ is preferably a divalent saturated hydrocarbon group with a saturated hydrocarbon ring. If $R_x$ is a saturated hydrocarbon group with a saturated hydrocarbon ring, the polyvalent carboxylic acid condensate will be able to form transparent cured epoxy resins. Multiple $R_x$ groups in the same molecule can be the same or different. The saturated hydrocarbon ring of $R_x$ can be optionally substituted with a halogen atom or a straight-chain or branched hydrocarbon group. A hydrocarbon group substituting the saturated hydrocarbon ring is preferably a saturated hydrocarbon group. The saturated hydrocarbon ring can be a monocycle or a fused ring, polycyclo ring, spiro ring or ring cluster comprising two or more rings. The number of carbons in $R_x$ is preferably 3-15.

$R_x$ is a group derived by removing a carboxyl group from the polyvalent carboxylic acid used as the monomer to obtain the component (polymer) represented by formula (1). The polyvalent carboxylic acid used as the monomer preferably has a higher boiling point than the reaction temperature for polycondensation.

More specifically, $R_x$ is preferably a divalent group derived by removing a hydrogen from a cyclic aliphatic hydrocarbon selected from among cyclobutane, cyclopentane, cyclohexane, cycloheptane, cyclooctane, norbornane, dicyclopentadiene, adamantane, naphthalene hydride and biphenyl hydride. If $R_x$ is one of these groups, a more notable effect of obtaining a transparent cured product with low coloration due to heating will be obtained. These cyclic saturated hydrocarbons can be optionally substituted with halogen atoms or straight-chain or branched hydrocarbon groups (preferably saturated hydrocarbon groups).

Most preferably, $R_x$ is a group derived by removing a carboxyl group from 1,2-cyclohexanedicarboxylic acid, 1,3-cyclohexanedicarboxylic acid, 1,4-cyclohexanedicarboxylic acid, or one of their derivatives. That is, $R_x$ is preferably a divalent group represented by the following formula (10). In formula (10), m represents an integer of 0-4. $R_z$ represents a halogen atom or a straight-chain or branched C1-4 hydrocarbon group. When m is 2-4, the multiple $R_z$ groups can be the same or different and can even be linked together to form a ring.

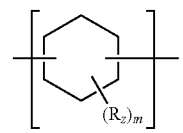

(10)

$R_y$ as the end groups in formula (1) each represent a monovalent hydrocarbon group optionally substituted with an acid anhydride or carboxylic acid ester group. The two $R_y$ groups can be the same or different. $R_y$ can also be a monovalent group derived by removing a carboxyl group from a straight-chain, branched or cyclic C2-15 aliphatic or aromatic monocarboxylic acid (benzoic acid or the like).

$R_y$ is preferably a monovalent group represented by the following chemical formula (20), or a monovalent group derived by removing a hydrogen from a cyclic aliphatic hydrocarbon selected from among cyclobutane, cyclopentane, cyclohexane, cycloheptane, cyclooctane, norbornane, dicyclopentadiene, adamantane, naphthalene hydride and biphenyl hydride. If $R_y$ is one of these groups, a more notable effect of obtaining a cured product with low coloration due to heating will be obtained. Also, if $R_y$ is one of these groups it will be possible to lower the carboxylic acid residue concentration in the polyvalent carboxylic acid condensate while also preventing molecular weight dispersion.

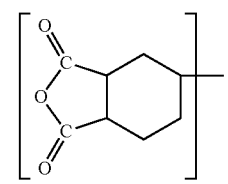

(20)

$R_x$ can be a divalent group represented by formula (10) above while $R_y$ is a monovalent group represented by chemical formula (20) above. That is, the polyvalent carboxylic acid condensate of this embodiment can comprise a component represented by the following formula (1a) as the component represented by formula (1).

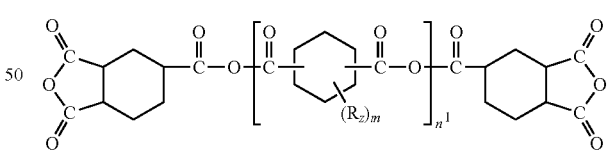

(1a)

The symbol $n^1$ in formulas (1) and (1a) each represent an integer of 1 or greater, and preferably an integer of 1-200.

The number-average molecular weight Mn of the polyvalent carboxylic acid condensate is preferably 200-20000, more preferably 300-20000 and even more preferably 300-10000. If Mn is less than 200 the viscosity will be too low, tending to interfere with inhibiting resin smudge during transfer molding of the thermosetting resin composition, while if it is greater than 20000 the compatibility with the epoxy resin can be reduced, thus lowering the flow property during transfer molding of the thermosetting resin composition.

The number-average molecular weight Mn for the purpose of the invention is the value obtained by measurement by gel permeation chromatography (GPC) using a calibration curve based on standard polystyrene, under the following conditions.
(GPC Conditions)
Pump: L-6200 (trade name of Hitachi, Ltd.).
Columns: TSKgel-G5000HXL and TSKgel-G2000HXL (trade names of Tosoh Corp.)
Detector: Model L-3300RI (trade name of Hitachi, Ltd.).
Eluent: tetrahydrofuran
Measuring temperature: 30° C.
Flow rate: 1.0 mL/min The polyvalent carboxylic acid condensate of this embodiment can be obtained by dehydrating condensation in a reaction mixture containing a polyvalent carboxylic acid and a monocarboxylic acid used as necessary. For example, it can be obtained by a method comprising a step of intermolecular dehydrating condensation between carboxyl groups of a reaction mixture containing a polyvalent carboxylic acid represented by the following formula (5) and a monocarboxylic acid represented by the following formula (6).

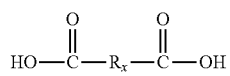

(5)

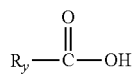

(6)

The dehydrating condensation reaction mixture comprises, for example, a polyvalent carboxylic acid and monocarboxylic acid, and a dehydrating agent that dissolves them, selected from among acetic anhydride or propionic anhydride, acetyl chloride, aliphatic acid chlorides, organic bases (trimethylamine and the like). For example, the reaction mixture is circulated for 5-60 minutes under a nitrogen atmosphere, and then the temperature of the reaction mixture is raised to 180° C. for polycondensation in an open system under a nitrogen stream, distilling off the produced acetic acid and water. When no further volatilizing components are observed, polycondensation is continued in a molten state while reducing the pressure in the reactor with a temperature of 180° C. for 3 hours, and more preferably 8 hours. The produced polyvalent carboxylic acid condensate can be purified by recrystallization or reprecipitation using an aprotic solvent such as acetic anhydride. During the dehydrating condensation reaction, the reaction conditions can be appropriately adjusted to obtain the target ICI cone-plate viscosity, number-average molecular weight and softening point, and there is no limitation to the reaction conditions described here.

The polyvalent carboxylic acid condensate obtained by this method can contain by-products including condensation products between the two monocarboxylic acid molecules of formula (6), condensation products of the polyvalent carboxylic acid of formula (5) and the monocarboxylic acid of formula (6), unreacted polyvalent carboxylic acid and monocarboxylic acid, and acid anhydrides produced by condensation reaction between the reagents such as acetic anhydride and propionic anhydride and the polyvalent carboxylic acid or monocarboxylic acid. These by-products can be removed by purification, or they can be used in the mixture as curing agents.

The ICI cone-plate viscosity, number-average molecular weight and softening point of the polyvalent carboxylic acid condensate used for the invention can be adjusted for the desired purpose by varying the charging compositional ratio of the polyvalent carboxylic acid and monocarboxylic acid before condensation reaction. A higher proportion of polyvalent carboxylic acid can increase the ICI cone-plate viscosity, number-average molecular weight and softening point. However, this tendency based on the condensation reaction conditions is not always exhibited, and factors such as the dehydrating condensation reaction conditions including the reaction temperature, degree of pressure reduction and reaction time must also be considered.

The softening point of the polyvalent carboxylic acid condensate is preferably 20-200° C., more preferably 20-130° C. and even more preferably 30-90° C. This will result in satisfactory dispersibility and workability when two roll mills or the like are used to disperse an inorganic filler in the resin composition comprising the polyvalent carboxylic acid condensate. Excellent inorganic filler dispersibility is especially important for a thermosetting resin composition for transfer molding. From the viewpoint of kneadability during production of the thermosetting resin composition using a roll mill, the softening point of the polyvalent carboxylic acid condensate is preferably 30-80° C. and more preferably 30-50° C. A softening point of below 20° C. can reduce the handleability, kneadability and dispersibility during production of the thermosetting resin composition, thus making it difficult to effectively inhibit resin smudge during transfer molding. A softening point of above 200° C. can result in residual molten curing agent in the resin composition after heating at 100-200° C. in transfer molding, thus making it difficult to obtain a homogeneous compact. The softening point of the polyvalent carboxylic acid condensate can be adjusted to the desired range by selecting the main chain structure and varying the number-average molecular weight. Generally speaking, using a long-chain divalent carboxylic acid as a monomer can lower the softening point, while introducing a highly polar structure can lower the softening point. The softening point can also usually be lowered with an increased number-average molecular weight.

When transparency and photoreflectance are not particularly required and the purpose is to inhibit burrs after transfer molding, the polyvalent carboxylic acid condensate can be an aromatic carboxylic acid compound that exhibits coloring at both ends with ordinary heating.

When a transfer-molded lead frame is plated as a post-step, a resin soiling-removal step can be added to the production process to improve the solder wettability, plating property and die bond paste adhesive force of the metal surface exposed on the photosemiconductor element mounting board. An example of a removal step is a method of carrying out electrolytic degreasing treatment and dip degreasing treatment steps, followed by removal of the soiling components by high-pressure water rinsing or media blasting, or with an air gun. Such a step is known as a "deflush step". However, a method of exposing the board to a strongly alkaline chemical solution can be employed in removal steps involving electrolytic degreasing treatment and dip degreasing treatment. In such cases, the resin portions on the lead frame can dissolve in the chemical solution, impairing the outer appearance of the product.

A polyvalent carboxylic acid condensate wherein the end groups ($R_y$ in formula (1)) are aromatic carboxylic acid compounds, such as the compound represented by the following formula (X), is preferred because it can be more resistant to dissolution of the resin portions upon exposure to alkaline degreasing solutions, and to the consequent outer appearance impairment.

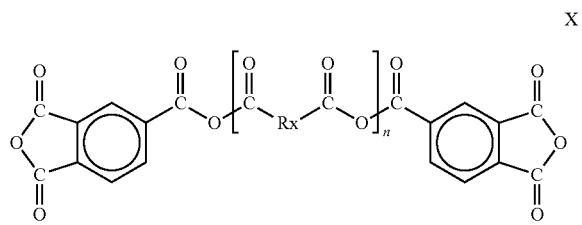

(In formula (X), $R_x$ represents a divalent group with an aliphatic hydrocarbon ring, wherein the aliphatic hydrocarbon ring is optionally substituted with a halogen atom or a straight-chain or branched hydrocarbon group, multiple $R_x$ groups in the same molecule can be the same or different, and n represents an integer of 1 or greater.)

The polyvalent carboxylic acid condensate content in the curable resin composition of this embodiment is preferably 10-100 wt %, more preferably 20-70 wt % and even more preferably 20-50 wt % based on the total weight of the (B) curing agent.

The (B) curing agent can further contain an acid anhydride formed by ring-closing condensation of a polyvalent carboxylic acid in the molecule. In this case, the equivalent ratio of epoxy groups in the (A) epoxy resin and polyacid anhydride groups in the (B) curing agent that are reactive with epoxy groups is preferably between 1:0.3 and 1:1.2. This can further minimize resin smudge during molding of the thermosetting resin composition of the invention.

In the thermosetting resin composition of this embodiment, a curing agent that is commonly used with epoxy resin molding materials for electronic part sealing can be used together with the polyvalent carboxylic acid condensate as the (B) curing agent. Such curing agents are not particularly restricted so long as they react with epoxy resins, but colorless or pale yellow agents are preferred. Examples of such curing agents include acid anhydride-based curing agents, isocyanuric acid derivative-based curing agents and phenol-based curing agents. Examples of acid anhydride-based curing agents include phthalic anhydride, maleic anhydride, trimellitic anhydride, pyromellitic anhydride, hexahydrophthalic anhydride, tetrahydrophthalic anhydride, methylnadic anhydride, nadic anhydride, glutaric anhydride, dimethylglutaric anhydride, diethylglutaric anhydride, succinic anhydride, methylhexahydrophthalic anhydride and methyltetrahydrophthalic anhydride. As isocyanuric acid derivatives there can be mentioned 1,3,5-tris(1-carboxymethyl)isocyanurate, 1,3,5-tris(2-carboxyethyl)isocyanurate, 1,3,5-tris(3-carboxypropyl)isocyanurate and 1,3-bis(2-carboxyethyl)isocyanurate. Preferred among these curing agents are phthalic anhydride, trimellitic anhydride, hexahydrophthalic anhydride, tetrahydrophthalic anhydride, methylhexahydrophthalic anhydride, methyltetrahydrophthalic anhydride, glutaric anhydride, dimethylglutaric anhydride, diethylglutaric anhydride and 1,3,5-tris(3-carboxypropyl)isocyanurate. These curing agents can be used alone or in combinations of two or more. When such compatible curing agents are included, the mixing ratio with the polyvalent carboxylic acid condensate is preferably adjusted to modify the overall viscosity of the (B) curing agents.

These compatible curing agents preferably have molecular weights of 100-400. Anhydrides having all of the aromatic ring unsaturated bonds hydrogenated are preferred over acid anhydrides having aromatic rings such as trimellitic anhydride or pyromellitic anhydride. As acid anhydride-based curing agents there can be used acid anhydrides that are commonly used as starting materials for polyimide resins.

The content of the (B) curing agent in the thermosetting resin composition of the invention is preferably 1-150 parts by weight with respect to 100 parts by weight of the (A) epoxy resin, and from the viewpoint of inhibiting resin smudge it is more preferably 50-120 parts by weight.

The (B) curing agent preferably has, with respect to 1 equivalent of epoxy groups in the (A) epoxy resin, 0.5-0.9 equivalent and more preferably 0.7-0.8 equivalent of active groups (acid anhydride or hydroxyl groups) in the (B) curing agent that can react with the epoxy groups. With less than 0.5 equivalent of active groups, the thermosetting resin composition curing speed will be slowed and the glass transition temperature of the obtained cured product will be reduced, making it difficult to obtain an adequate elastic modulus.

With greater than 0.9 equivalent of active groups, the post-curing strength can be lower.

<(C) Curing Accelerator>

The thermosetting resin composition of the invention can contain a (C) curing accelerator if necessary. The (C) curing accelerator is not particularly limited so long as it has a catalyst function that promotes curing reaction between components (A) and (B). Examples of curing accelerators include amine compounds, imidazole compounds, organo-phosphorus compounds, alkali metal compounds, alkaline earth metal compounds and quaternary ammonium salts. Of these curing accelerators, amine compounds, imidazole compounds and organo-phosphorus compounds are preferably used. Examples of amine compounds include 1,8-diaza-bicyclo(5,4,0)undecene-7, triethylenediamine and tri-2,4,6-dimethylaminomethylphenol. Examples of imidazole compounds include 2-ethyl-4-methylimidazole. Examples of organo-phosphorus compounds include triphenylphosphine, tetraphenylphosphoniumtetraphenyl borate, tetra-n-butylphosphonium-o,o-diethylphosphorodithioate, tetra-n-butylphosphonium-tetrafluoroborate and tetra-n-butylphosphonium-tetraphenyl borate. These curing accelerators can be used alone or in combinations of two or more.

The content of the (C) curing accelerator is preferably 0.01-8 parts by weight and more preferably 0.1-3 parts by weight with respect to 100 parts by weight of the (A) epoxy resin. With a curing accelerator content of less than 0.01 part by weight it can not be possible to obtain a sufficient curing acceleration effect, and with a content of greater than 8 parts by weight the obtained compact can exhibit coloration;

<(D) White Pigment>

When used as a white molding resin for use in a photo-semiconductor device, the thermosetting resin composition of the invention preferably further comprises (D) a white pigment. The (D) white pigment used can be any known one, without any particular restrictions. Examples of white pigments include alumina, magnesium oxide, antimony oxide, titanium oxide, zirconium oxide and inorganic hollow particles. Any of these can be used alone or in mixtures of two or more. Examples of inorganic hollow particles include sodium silicate glass, aluminum silicate glass, sodium borosilicate glass and white sand. The particle size of the white pigment is preferably a center particle size of 0.1-50 μm, as a center particle size of less than 0.1 μm can promote aggregation and lower the dispersibility of the particles, while a size of greater than 50 μm can make it difficult to obtain adequate reflectance properties for cured products of the thermosetting resin composition.

The (D) white pigment content is not particularly restricted but is preferably 10-85 vol % and more preferably 20-75 vol % with respect to the total thermosetting resin composition. A content of less than 10 vol % can make it difficult to obtain adequate photoreflectance properties for the cured thermosetting resin composition, while a content of greater than 85 vol % can lower the moldability of the thermosetting resin composition.

When the thermosetting resin composition contains an inorganic filler as described hereunder in addition to the (D) white pigment, the total content of the (D) white pigment and inorganic filler can be 10-85 vol % with respect to the total thermosetting resin composition, to allow further improvement in the moldability of the thermosetting resin composition.

<Other Components>
(Inorganic Filler)

The thermosetting resin composition preferably contains an inorganic filler to adjust the moldability. The same inorganic fillers can be used as for the white pigment. Examples of inorganic fillers include silica, antimony oxide, titanium oxide, aluminum hydroxide, magnesium hydroxide, barium sulfate, magnesium carbonate, barium carbonate, alumina, mica, beryllia, barium titanate, potassium titanate, strontium titanate, calcium titanate, aluminum carbonate, aluminum silicate, calcium carbonate, calcium silicate, magnesium silicate, silicon nitride, boron nitride, clays such as calcined clay, talc, aluminum borate, aluminum borate and silicon carbide. From the viewpoint of thermal conductivity, photoreflectance, moldability and flame retardance, the inorganic filler is preferably a mixture of two or more selected from the group consisting of silica, alumina, magnesium oxide, antimony oxide, titanium oxide, zirconium oxide, aluminum hydroxide and magnesium hydroxide. The mean particle size of the inorganic filler is preferably 1-100 μm and more preferably 1-40 μm from the viewpoint of improving packing with the white pigment. The content of the inorganic filler in the thermosetting resin composition of this embodiment is preferably 1-1000 parts by weight and more preferably 1-800 parts by weight with respect to 100 parts by weight as the total of component (A) and component (B).

(Coupling Agent)

The thermosetting resin composition preferably contains an added coupling agent from the viewpoint of enhancing the adhesion between the thermosetting resin components (A)-(C), the (D) white pigment and the inorganic filler which is added as necessary. Examples of coupling agents include silane coupling agents and titanate-based coupling agents, without any particular restrictions. As common silane coupling agents there can be mentioned epoxysilane-based, aminosilane-based, cationic silane-based, vinylsilane-based, acrylsilane-based and mercaptosilane-based agents, as well as their complex systems, and they can be used in any desired amounts. The coupling agent content is preferably no greater than 5 wt % with respect to the total thermosetting resin composition.

The thermosetting resin composition of this embodiment can contain additives such as antioxidants, release agents and ion scavengers, as necessary.

[Method for Producing Thermosetting Resin Composition]

The thermosetting resin composition of this embodiment can be obtained by uniformly dispersing and mixing each of the aforementioned components, without any particular restrictions on the means or conditions. A common method for producing thermosetting resin compositions is a method involving kneading the components with an extruding machine, kneader, roll, extruder or the like, cooling the kneaded blend, and pulverizing it. Kneading of the components is preferably carried out in a molten state from the viewpoint of improving the dispersibility. The kneading conditions can be appropriately set depending on the type and amount of each component, with kneading at 15-100° C. for 5-40 minutes being preferred and kneading at 20-100° C. for 10-30 minutes being more preferred. If the kneading temperature is below 15° C., kneading of each component will be more difficult, tending to lower the dispersibility, while if it is above 100° C. the resin composition will be more highly molecularized, potentially hardening the resin composition. If the kneading time is shorter than 5 minutes, resin burrs can be generated during transfer molding. If the kneading time is longer than 40 minutes, the resin composition will be more highly molecularized, potentially hardening the resin composition.

The thermosetting resin composition of the invention can be produced by a pre-mixing step in which the (A) epoxy resin and (B) curing agent are pre-mixed, followed by addition of the other components and kneading with a roll mill or extruder. The pre-mixing step is preferred when, for example, either or both the (A) epoxy resin and (B) curing agent are liquid at 0-35° C., or have low viscosity of below 10 mPa·s at 100-200° C. The thermosetting resin composition obtained by pre-mixing using the (A) epoxy resin and (B) curing agent has improved storage stability and exhibits excellent moldability during transfer molding.

The viscosity of the pre-mixture in the pre-mixing step is preferably 10-10000 mPa·s at 100-150° C., and the viscosity is preferably 10-10000 mPa·s at 100° C. A viscosity of lower than 10 mPa·s can generate burrs during transfer molding, while a viscosity of higher than 10000 mPa·s can lower the flow property during molding, thus impeding flow of the thermosetting resin composition into the die and reducing the moldability.

From the viewpoint of preventing increase in viscosity by generation of precipitates, the mixing conditions in the pre-mixing step, are preferably adjusted to avoid precipitation such as gelling of the cured reaction product of the (A) epoxy resin and (B) curing agent and consequent opacity of the pre-mixture due to precipitates. "Opacity due to precipitates" indicates scattering in the visible light range of the electromagnetic spectrum. More specifically, it indicates an absence of fine particles as scatter centers that produce Rayleigh scattering, Mie scattering and diffraction scattering of light.

In the pre-mixing step, specifically, a method can be employed in which 100 parts by weight of the (A) epoxy resin and 120 parts by weight of the (B) curing agent are weighed out into a heat-resistant glass container, and the mixture container is heated at 35-180° C. using a heater with a fluid such as silicone oil or water as the medium. The heating method is not limited to this method, and a thermocouple, electromagnetic wave irradiation or the like can be used instead, or ultrasonic waves can be utilized to promote dissolution.

A portion of the (A) epoxy resin and (B) curing agent that are to be combined in the thermosetting resin composition can also be pre-mixed in the pre-mixing step. Specifically, for production of a thermosetting resin composition comprising 100 parts by weight of the (A) epoxy resin and 120 parts by weight of the (B) curing agent, first 50 parts by weight of the (A) epoxy resin and 120 parts by weight of the (B) curing agent are weighed out into a heat-resistant glass container and the mixture container is heated at 35-180° C. using a heater with a fluid such as silicone oil or water as the medium, to obtain a pre-mixture. The obtained pre-mixture can then be mixed with the remaining 50 parts by weight of the (A) epoxy resin and the (C) curing accelerator and other components, by roll kneading or the like, to produce a thermosetting resin composition.

The thermosetting resin composition of this embodiment can be pressure molded into a tablet at near room temperature (15-30° C.), and preferably the optical reflectance at a wavelength of 350-800 nm after thermosetting is 80% or greater. The pressure molding can be carried out under conditions of, for example, about 5-50 MPa for 1-5 seconds at room temperature. If the optical reflectance is less than 80% it can not be possible to sufficiently contribute to improved luminance of the photosemiconductor device; a more preferred optical reflectance range is 90% or greater.

The thermosetting resin composition of the invention preferably has a burr length of no greater than 5 mm when subjected to transfer molding under conditions with a molding temperature of 100° C.-200° C., a molding pressure of 5-20 MPa and a molding time of 60-180 seconds. If the burr length is greater than 5 mm, resin smudge can occur in the opening (recess) which serves as the photosemiconductor element mounting region during fabrication of a photosemiconductor element mounting board, causing problems during mounting of photosemiconductor elements, and potentially hampering electrical connection between photosemiconductor elements and metal wirings. From the viewpoint of workability during semiconductor device production, the burr length is more preferably no greater than 3 mm and even more preferably no greater than 1 mm.

The thermosetting resin composition of this embodiment is useful for a variety of purposes including electrical insulating materials, photosemiconductor sealing materials, adhesive materials, coating materials and transfer molding epoxy resin molding materials, which require high transparency and heat resistance.

[Epoxy Resin Molding Material]

The epoxy resin molding material of the invention is an epoxy resin molding material comprising (A) an epoxy resin and (B) a curing agent, wherein the (B) curing agent contains the aforementioned polyvalent carboxylic acid condensate.

[Photosemiconductor Element Mounting Board]

The semiconductor element mounting board of the invention has a recess composed of the bottom face and the wall faces, wherein the bottom face of the recess is the photosemiconductor element mounting section and at least parts of the wall faces of the recess are made of a cured thermosetting resin composition or epoxy resin molding material of the invention. FIG. 1 is a perspective view showing an embodiment of a photosemiconductor element mounting board of the invention. The photosemiconductor element mounting board 110 comprises a metal wiring 105 on which a Ni/Ag plating 104 is formed, and a reflector 103, and has a recess 200 formed from the metal wiring 105 on which the Ni/Ag plating 104 is formed, and the reflector 103. That is, the bottom face of the recess 200 is composed of the metal wiring 105 on which the Ni/Ag plating 104 is formed, while the wall face of the recess is composed of the reflector 103, the reflector 103 being a compact comprising the cured thermosetting resin composition of the invention.

Figure 2:
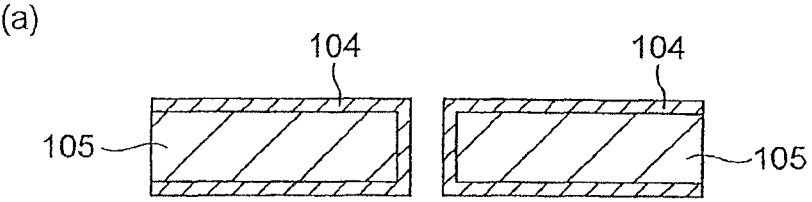
FIG. 2 is a schematic diagram showing an embodiment of a step for production of a photosemiconductor element mounting board of the invention.
Figure 2:
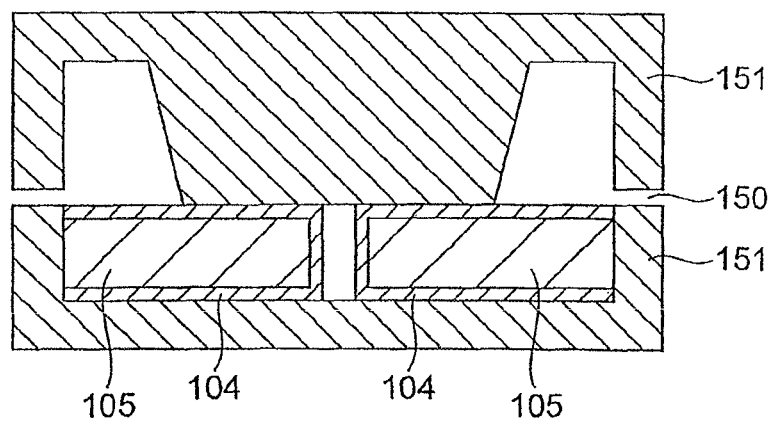
Figure 2:
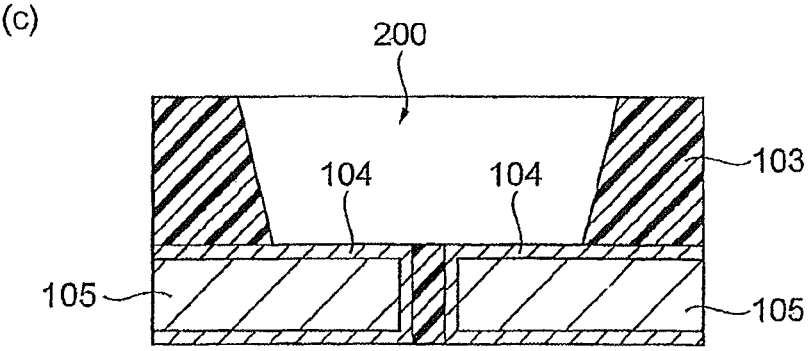

There are no particular restrictions on the method for producing the photosemiconductor element mounting board of the invention, and for example, it can be produced by transfer molding using a thermosetting resin composition according to the invention. FIG. 2 is a schematic diagram showing an embodiment of a step for production of a photosemiconductor element mounting board of the invention. The photosemiconductor element mounting board can be produced, for example, by a step of forming a metal wiring 105 from a metal foil by a known method such as punching or etching and covering it with a Ni/Ag plating 104 by electroplating (FIG. 2(a)), followed by a step of placing the metal wiring 105 on a die 151 having a prescribed shape and injecting the thermosetting resin composition of the invention from the resin sprue 150 of the die 151 and performing transfer molding under prescribed conditions (FIG. 2(b)), further followed by a step of removing the die 151 (FIG. 2(c)). Thus, a photosemiconductor element mounting region (recess) 200 is formed surrounding a reflector 103 made of a cured thermosetting resin composition, on the photosemiconductor element mounting board. The transfer molding conditions are preferably 60-120 seconds with a mold temperature of 170-200° C. and a molding pressure of 0.5-20 MPa, and 1-3 hours with an after-cure temperature of 120° C.-180° C.

[Photosemiconductor Device]

The photosemiconductor device of the invention comprises the aforementioned photosemiconductor element mounting board, a photosemiconductor element provided in the recess of the photosemiconductor element mounting board, and a sealing resin section which fills the recess to seal the photosemiconductor element.

Figure 3:
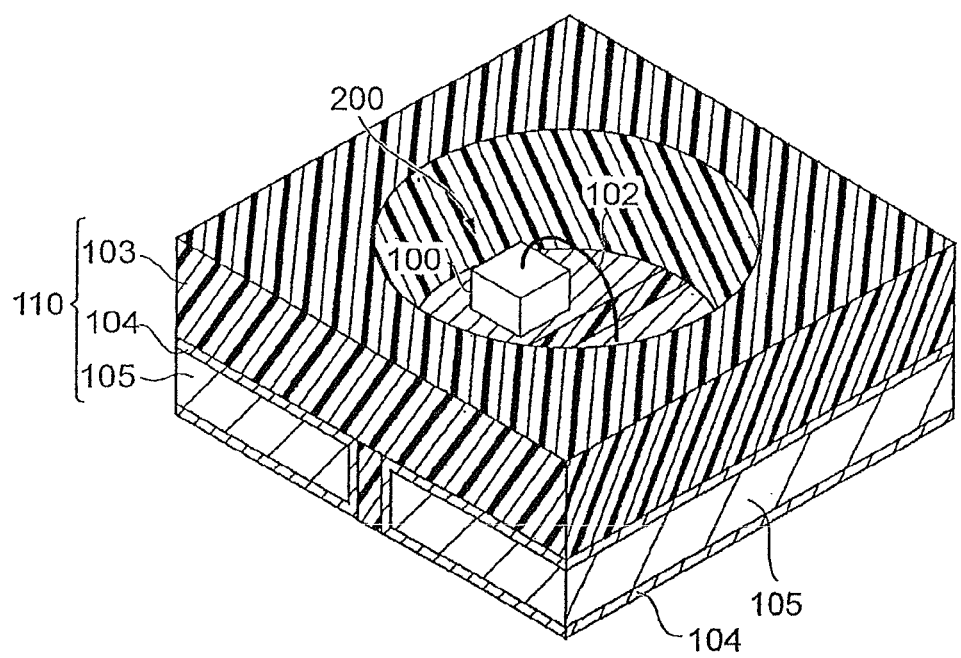
FIG. 3 is a perspective view showing an embodiment of the mounted state of a photosemiconductor element on a photosemiconductor element mounting board of the invention.
Figure 4:
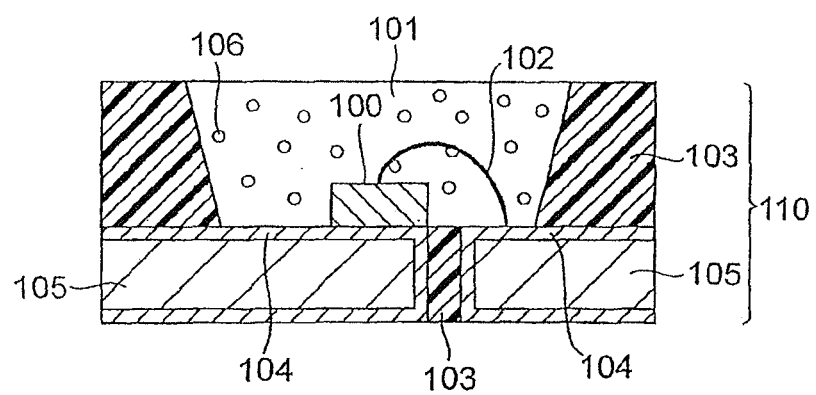
FIG. 4 is a schematic cross-sectional view showing an embodiment of a photosemiconductor device according to the invention.
Figure 5:
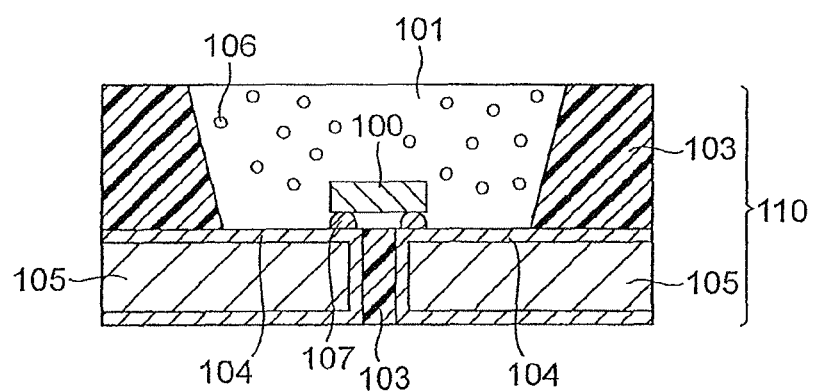
FIG. 5 is a schematic cross-sectional view showing an embodiment of a photosemiconductor device according to the invention.

FIG. 3 is a perspective view showing an embodiment of the mounted state of a photosemiconductor element 100 on a photosemiconductor element mounting board 110 of the invention. As shown in FIG. 3, the photosemiconductor element 100 is mounted on a prescribed location of the photosemiconductor element mounting region (recess) 200 of the photosemiconductor element mounting board 110, and it is electrically connected by the metal wiring 105 and a bonding wire 102. FIGS. 4 and 5 are schematic cross-sectional views each showing an embodiment of a photosemiconductor device according to the invention. As seen in FIGS. 4 and 5, the photosemiconductor device comprises a photosemiconductor element mounting board 110, a photosemiconductor element 100 provided at a prescribed location inside the recess 200 of the photosemiconductor element mounting board 110, and a sealing resin section comprising a transparent sealing resin 101 containing a fluorescent material 106, which fills the recess 200 to seal the photosemiconductor element, wherein the photosemiconductor element 100 is electrically connected with the metal wiring 105 on which the Ni/Ag plating 104 is formed by a bonding wire 102 or solder bump 107.

Figure 6:
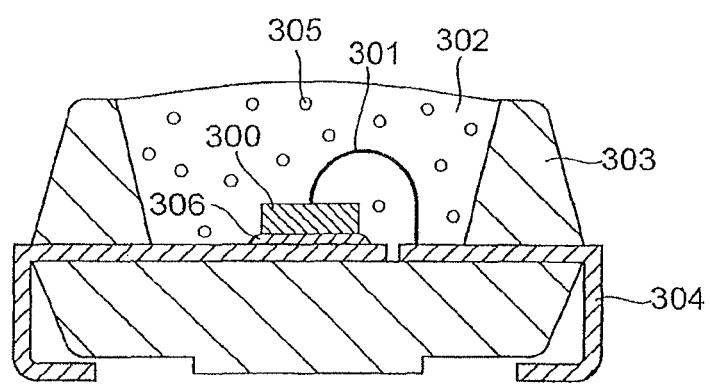
FIG. 6 is a schematic cross-sectional view showing an embodiment of a photosemiconductor device according to the invention.

FIG. 6 is also a schematic cross-sectional view showing an embodiment of a photosemiconductor device according to the invention. In the photosemiconductor device shown in FIG. 6, an LED element 300 is positioned on a lead 304 on which a reflector 303 is formed, via a die bond material 306, and the LED element 300 and lead 304 are electrically connected by a bonding wire 301, the LED element 300 being sealed by a transparent sealing resin 302 containing a fluorescent material 305.

[Polyvalent Carboxylic Acid Condensate]

The polyvalent carboxylic acid condensate of the invention will usually be composed of a plurality of components with different polymerization degrees, and it can contain a plurality of components with different repeating units and end groups. The polyvalent carboxylic acid condensate of this embodiment also preferably contains a component represented by the following formula (1) as a major component. The proportion of the component of formula (1) is at least 10 wt % based on the total weight of the polyvalent carboxylic acid condensate.

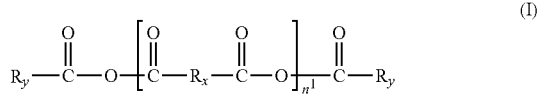

(I)

In formula (I), $R_x$ is preferably a divalent saturated hydrocarbon group with a saturated hydrocarbon ring. If $R_x$ is a saturated hydrocarbon group with a saturated hydrocarbon ring, the polyvalent carboxylic acid condensate will be able to form transparent cured epoxy resins. Multiple $R_x$ groups in the same molecule can be the same or different. The saturated hydrocarbon ring of $R_x$ can be optionally substituted with a halogen atom or a straight-chain or branched hydrocarbon group. A hydrocarbon group substituting the saturated hydrocarbon ring is preferably a saturated hydrocarbon group. The saturated hydrocarbon ring can be a monocycle or a fused ring, polycyclo ring, spiro ring or ring cluster comprising two or more rings. The number of carbons in $R_x$ is preferably 3-15.

$R_x$ is a group derived by removing a carboxyl group from the polyvalent carboxylic acid used as the monomer to obtain a polymer represented by formula (I). The polyvalent carboxylic acid used as the monomer preferably has a higher boiling point than the reaction temperature for polycondensation.

More specifically, $R_x$ is preferably a divalent group derived by removing a hydrogen from a cyclic aliphatic hydrocarbon selected from among cyclobutane, cyclopentane, cyclohexane, cycloheptane, cyclooctane, norbornane, dicyclopentadiene, adamantane, naphthalene hydride and biphenyl hydride. If $R_x$ is one of these groups, a more notable effect of obtaining a transparent cured product with low coloration due to heating will be obtained. These cyclic saturated hydrocarbons can be optionally substituted with halogen atoms or straight-chain or branched hydrocarbon groups (preferably saturated hydrocarbon groups).

Most preferably, $R_x$ is a group derived by removing a carboxyl group from 1,2-cyclohexanedicarboxylic acid, 1,3-cyclohexanedicarboxylic acid, 1,4-cyclohexanedicarboxylic acid, or one of their derivatives. That is, $R_x$ is preferably a divalent group represented by formula (10) above.

$R_y$ as the end groups in formula (I) each represent a monovalent hydrocarbon group optionally substituted with an acid anhydride or carboxylic acid ester group. The two $R_y$ groups can be the same or different. $R_y$ can also be a monovalent group derived by removing a carboxyl group from a straight-chain, branched or cyclic C2-15 aliphatic or aromatic monocarboxylic acid (benzoic acid or the like).

$R_y$ is preferably a monovalent group represented by chemical formula (20) above, or a monovalent group derived by removing a hydrogen from a cyclic aliphatic hydrocarbon selected from among cyclobutane, cyclopentane, cyclohexane, cycloheptane, cyclooctane, norbornane, dicyclopentadiene, adamantane, naphthalene hydride and biphenyl hydride. If $R_y$ is one of these groups, a more notable effect of obtaining a transparent cured product with low coloration due to heating will be obtained.

$R_x$ can be a divalent group represented by formula (10) above while $R_y$ is a monovalent group represented by chemical formula (20) above. That is, the polyvalent carboxylic acid condensate of this embodiment can comprise a component represented by formula (1a) above as the component represented by formula (I).

In formulas (I) and (1a), $n^1$ is an integer of 1 or greater, and preferably an integer of 1-200.

The polyvalent carboxylic acid condensate can further include a component represented by the following formula (2). A component of formula (2) will sometimes be produced as a by-product during polycondensation of the polyvalent carboxylic acid. Formula (2) shows a carbonyl carbon and oxygen atom in the repeating unit directly bonding to form a cyclic structure.

(2)

The number-average molecular weight Mn of the polyvalent carboxylic acid condensate is preferably 300-20000. The number-average molecular weight Mn of the polyvalent carboxylic acid condensate can also be in a range of 300-5000. A number-average molecular weight Mn of less than 300 can result in excessively low viscosity, while greater than 20000 can result in low compatibility with the epoxy resin.

The viscosity of the polyvalent carboxylic acid condensate as measured with an ICI cone-plate Brookfield viscometer is preferably 10-30000 mPa·s in the range of 100-150° C. If the viscosity of the polyvalent carboxylic acid condensate is within this specified range, satisfactory moldability, with minimal burr generation, will be obtained when the polyvalent carboxylic acid condensate-containing epoxy resin composition is used for transfer molding, for example. The viscosity of the polyvalent carboxylic acid condensate can be measured using an ICI cone-plate Brookfield viscometer by Research Equipment (London) Ltd., for example.

The softening point of the polyvalent carboxylic acid condensate is preferably 20-200° C., more preferably 30-130° C. and even more preferably 30-90° C. This will result in satisfactory dispersibility and workability when two roll mills or the like are used to disperse an inorganic filler in the resin composition comprising the polyvalent carboxylic acid condensate. Excellent dispersibility of the inorganic filler is especially important for epoxy resin compositions for transfer molding.

The polyvalent carboxylic acid condensate of the invention can be obtained, for example, by a method comprising a step of intermolecular dehydrating condensation between carboxyl groups of a reaction mixture containing a polyvalent carboxylic acid represented by formula (5) above and a monocarboxylic acid represented by formula (6) above.

The dehydrating condensation reaction mixture comprises, for example, a polyvalent carboxylic acid and monocarboxylic acid, and a dehydrating agent that dissolves them, selected from among acetic anhydride or propionic anhydride, acetyl chloride, aliphatic acid chlorides, organic bases (trimethylamine and the like). For example, the reaction mixture is circulated for 5-30 minutes under a nitrogen atmosphere, and then the temperature of the reaction mixture is raised to 180° C. for polycondensation in an open system under a nitrogen stream, distilling off the produced acetic acid and water. When no further volatilizing components are observed, polycondensation is continued in a molten state while reducing the pressure in the reactor at a temperature of 180° C. for 3 hours, and more preferably 1 hour. The produced polyvalent carboxylic acid condensate can be purified by recrystallization or reprecipitation using an aprotic solvent such as acetic anhydride.

The polyvalent carboxylic acid condensate obtained by this method can contain condensation products between the two monocarboxylic acid molecules of formula (6), condensation products of the polyvalent carboxylic acid of formula (5) and the monocarboxylic acid of formula (6), unreacted polyvalent carboxylic acid and monocarboxylic acid, and by-products including acid anhydrides, such as acetic anhydride and propionic anhydride, produced by condensation reaction between the reagents and the polyvalent carboxylic acid or monocarboxylic acid.

[Epoxy Resin Curing Agent]

The epoxy resin curing agent of this embodiment is an acid anhydride-based curing agent comprising a polyvalent carboxylic acid condensate and an acid anhydride compound that can be obtained by intramolecular dehydrating condensation between the carboxyl groups of a polyvalent carboxylic acid. The acid anhydride compound to be combined with the polyvalent carboxylic acid condensate can be one that is commonly used as an epoxy resin molding material for electronic part sealing, an epoxy resin molding material for photosemiconductor sealing, or the like. The acid anhydride compound used is not particularly restricted so long as it reacts with the epoxy resin, but it is preferably colorless or pale yellow.

The molecular weight of the acid anhydride compound is preferably 100-400. Anhydrides having all of the aromatic ring unsaturated bonds hydrogenated are preferred over acid anhydrides having aromatic rings such as trimellitic anhydride or pyromellitic anhydride. An acid anhydride compound commonly used as a starting material for polyimide resins can be used.

The acid anhydride compound can be, for example, at least one type selected from the group consisting of phthalic anhydride, maleic anhydride, trimellitic anhydride, pyromellitic anhydride, hexahydrophthalic anhydride, tetrahydrophthalic anhydride, methylnadic anhydride, nadic anhydride, glutaric anhydride, dimethylglutaric anhydride, diethylglutaric anhydride, succinic anhydride, methylhexahydrophthalic anhydride and methyltetrahydrophthalic anhydride. Preferred among these are phthalic anhydride, trimellitic anhydride, hexahydrophthalic anhydride, tetrahydrophthalic anhydride, methylhexahydrophthalic anhydride, methyltetrahydrophthalic anhydride, glutaric anhydride, dimethylglutaric anhydride and diethylglutaric anhydride.

The epoxy resin curing agent of this embodiment can include an isocyanuric acid derivative as an acid anhydride compound. As isocyanuric acid derivatives there can be mentioned acid anhydrides derived from 1,3,5-tris(1-carboxymethyl)isocyanurate, 1,3,5-tris(2-carboxyethyl)isocyanurate, 1,3,5-tris(3-carboxypropyl)isocyanurate or 1,3-bis(2-carboxyethyl)isocyanurate. These can be used alone or in combinations of two or more. Acid anhydrides derived from 1,3,5-tris(3-carboxypropyl)isocyanurate are preferably used among these.

The epoxy resin curing agent of this embodiment can further contain a phenol-based compound.

The polyvalent carboxylic acid condensate and acid anhydride compound are preferably compatible. That the "polyvalent carboxylic acid condensate and acid anhydride compound are compatible" means that the polyvalent carboxylic acid condensation product exhibits affinity for the acid anhydride compound, and their mixture can exist in a homogeneous state. More specifically, a mixture of the polyvalent carboxylic acid condensate and acid anhydride compound in a weight ratio of 1/1 can be heated at 120° C. to complete dissolution and stirred in that state, and then the mixture stationed for 30 minutes and a portion thereof taken and observed, to allow their compatibility to be judged based on whether their mixture is a transparent liquid without phase separation. If it is an opaque liquid due to phase separation, they are referred to as "insoluble". Even with a compatible combination, a longer time needed for dissolution will require more heat energy due to the longer heating time, which is disadvantageous in terms of productivity and cost.

The epoxy resin curing agent of this embodiment preferably contains the polyvalent carboxylic acid condensate at 10-70 wt % and the acid anhydride compound at 30-90 wt %, based on the total weight of the curing agent.

The epoxy resin curing agent of this embodiment can be obtained, for example, by a method comprising a mixing step in which the polyvalent carboxylic acid condensate, polyvalent carboxylic acid and acid anhydride compound are melted and mixed. Specifically, for example, a method can be employed in which the polyvalent carboxylic acid condensate and acid anhydride compound are combined using a known mixer, and if necessary are melt kneaded using a triple roll mill, extruder or the like. From the viewpoint of obtaining a transparent cured product, the mixture of the polyvalent carboxylic acid condensate and acid anhydride compound are preferably translucent.

In the mixing step, it is preferred for there to be no opacity due to precipitates. Viscosity increase is inhibited by production of precipitates. "No opacity due to precipitates" means no scattering in the visible light range of the electromagnetic spectrum. More specifically, the mixture can be considered to have "no opacity due to precipitates" if it lacks fine particles as scatter centers that produce Rayleigh scattering, Mie scattering and diffraction scattering of light. Opacity in the mixture can be confirmed, for example, by a method of weighing out 100 parts by weight of the polyvalent carboxylic acid condensate and 120 parts by weight of the acid anhydride compound into a heat-resistant glass container, and heating the container in a temperature range of 35° C.-180° C. using a heater with a fluid such as silicone oil or water as the medium. The heating method is not limited to this method, and a known method employing a thermocouple, electromagnetic wave irradiation or the like can be used instead, or ultrasonic waves can be utilized to further promote dissolution.

[Epoxy Resin Composition and its Cured Product]

The epoxy resin composition of this embodiment includes an epoxy resin and an epoxy resin curing agent. The epoxy resin used can be the same as the epoxy resin mentioned above.

The epoxy resin composition comprises the curing agent in a range for preferably 0.5-0.9 equivalent and more preferably 0.5-0.8 equivalent of active groups (acid anhydride groups or hydroxyl groups) in the curing agent that can react with the epoxy group, with respect to 1 equivalent of epoxy groups in the epoxy resin. With less than 0.5 equivalent of active groups, the epoxy resin composition curing speed will be slowed and the glass transition temperature and elastic modulus of the obtained cured product can be lowered. With greater than 0.9 equivalent of active groups, on the other hand, the post-curing strength can be lower.

The epoxy resin composition can further contain a curing catalyst (curing accelerator) from the viewpoint of enhancing the curability. The curing catalyst is not particularly restricted, and there can be used, for example, tertiary amines such as 1,8-diaza-bicyclo(5,4,0)undecene-7, triethylenediamine and tri-2,4,6-dimethylaminomethylphenol, imidazoles such as 2-ethyl-4-methylimidazole and 2-methylimidazole, phosphorus compounds such as triphenylphosphine, tetraphenylphosphoniumtetraphenyl borate, tetra-n-butylphosphonium-o,o-diethylphosphorodithioate, tetra-n-butylphosphonium-tetrafluoroborate and tetra-n-butylphosphonium-tetraphenyl borate, quaternary ammonium salts, organometallic salts, and derivatives of the foregoing. These can be used alone or in combinations. Tertiary amines, imidazoles and phosphorus compounds are preferred among these curing catalysts.

The proportion of the curing catalyst with respect to the epoxy resin is preferably 0.01-8 wt % and more preferably 0.1-3 wt %. If the curing catalyst proportion is less than 0.01 wt % the curing acceleration effect can be reduced, and if it exceeds 8 wt % the cured product coloration-inhibiting effect can be reduced.

The cured product formed by thermal curing of the epoxy resin composition preferably has high transmittance in the wavelength range from visible light to near ultraviolet light. It preferably has a transmittance of 70% or greater, more preferably 80% or greater and most preferably 90% or greater.

The epoxy resin composition and cured product of this embodiment is useful for a variety of purposes including electrical insulating materials, photosemiconductor sealing materials, adhesive materials, coating materials and transfer molding epoxy resin molding materials, which require high transparency and heat resistance.

[Polyamide Resin and Polyester Resin]

The polyvalent carboxylic acid condensate of the invention can be used as a starting material for a polyamide resin or polyester resin. A polyamide resin or polyester resin can be produced by polycondensation of the polyvalent carboxylic acid with a polyamine having two or more amino groups or a polyalcohol having two or more hydroxyl groups. The method of polymerizing the polyvalent carboxylic acid condensate with the polyamine or polyester can be a known polymerization method.

The polyamine combined with the polyvalent carboxylic acid condensate can be one that is commonly used as a polyamide resin starting material, and it preferably has minimal coloration. A C2-24 diamine will be used in most cases. As preferred examples of polyamines there can be mentioned aliphatic diamines such as ethylenediamine, trimethylenediamine, tetramethylenediamine, pentamethylenediamine, hexamethylenediamine, heptamethylenediamine, octamethylenediamine, nonamethylenediamine, decamethylenediamine, undecamethylenediamine, dodecamethylenediamine, tridecamethylenediamine, hexadecamethylenediamine octadecamethylenediamine and 2,2,4 (or 2,4,4)-trimethylhexamethylenediamine, alicyclic diamines such as cyclohexanediamine, methylcyclohexanediamine and bis-(4,4'-aminocyclohexyl)methane, and aromatic diamines such as xylylenediamine. These can be used as single compounds or as combinations of two or more compounds.

The polyalcohol combined with the polyvalent carboxylic acid condensate can be one that is commonly used as a polyester resin starting material, and it preferably has minimal coloration. A C2-24 dialcohol will be used in most cases. As specific examples of preferred polyalcohols there can be mentioned pentacyclic diols such as 1,2-, 1,3-cyclopentanediol, 1,2-, 1,3-cyclopentanedimethanol and bis(hydroxymethyl)tricyclo[5.2.1.0]decane, and hexacyclic diols such as 1,2-, 1,3-, 1,4-cyclohexanediol, 1,2-, 1,3-, 1,4-cyclohexanedimethanol and 2,2-bis-(4-hydroxycyclohexyl)propane. There can also be mentioned aliphatic diols such as ethylene glycol, propylene glycol, butylene glycol, trimethylene glycol, pentamethylene glycol, hexamethylene glycol, octamethylene glycol, decamethylene glycol, neopentyl glycol, diethylene glycol, polyethylene glycol, polytrimethylene ether glycol and polytetramethylene ether glycol, and aromatic diols such as xylylene glycol, 4,4'-hydroxybiphenyl, 2,2-bis(4'-hydroxyphenyl)propane, 2,2-bis(4'-β-hydroxyethoxyphenyl)propane and bis(4-hydroxyphenyl)sulfonebis (4-β-hydroxyethoxyphenyl)sulfonic acid. These can be used as single compounds or as combinations of two or more compounds.

The present invention is not in any way limited to the preferred embodiment described above.

EXAMPLES

The present invention will now be explained in detail by examples, with the understanding that the invention is not limited to the examples.

<Preparation of Polyvalent Carboxylic Acid Condensate 1>

Each of the repeating unit monomers and end monomers indicated in Synthesis Examples A1, A2, A3, A4, A5 and A6 were circulated in acetic anhydride for 5-60 minutes under a nitrogen atmosphere, and then the temperature was raised to 180° C., and the acetic acid and water produced by the reaction in an open system under a nitrogen stream were removed. When no further volatilizing components were detected, the pressure inside the reactor was reduced while conducting melt condensation at a temperature of 180° C. for 1-15 hours to obtain a polyvalent carboxylic acid condensate.

Synthesis Example A1

Repeating unit: 125 g of hydrogenated terephthalic acid (product of Tokyo Chemical Industry Co., Ltd.)
Ends: 126 g of hydrogenated 1,2-trimellitic anhydride (product of Mitsubishi Gas Chemical Co., Inc.)

Synthesis Example A2

Repeating unit: 218 g of hydrogenated terephthalic acid (product of Tokyo Chemical Industry Co., Ltd.)
Ends: 86 g of hydrogenated trimellitic anhydride (product of Mitsubishi Gas Chemical Co., Inc.)

Synthesis Example A3

Repeating unit: None
Ends: 100 g of hydrogenated 1,2-trimellitic anhydride (product of Mitsubishi Gas Chemical Co., Inc.)

Synthesis Example A4

Repeating unit: 125 g of hydrogenated isophthalic acid (product of Iwatani Gas Chemical Industry Co., Ltd.)
Ends: 126 g of hydrogenated 1,2-trimellitic anhydride (product of Mitsubishi Gas Chemical Co., Inc.)

Synthesis Example A5

Repeating unit: 226 g of hydrogenated naphtalene-1,10-dicarboxylic acid derived from hydrogenated naphtalene-1,10-dicarboxylic acid dimethyl ester (product of Iwatani Gas Chemical Industry Co., Ltd.)
Ends: 174 g of hydrogenated 1,2-trimellitic anhydride (product of Mitsubishi Gas Chemical Co., Inc.)

Synthesis Example A6

Repeating unit: 170 g of hydrogenated terephthalic acid (product of Tokyo Chemical Industry Co., Ltd.)
Ends: 195 g of trimellitic anhydride (product of Mitsubishi Gas Chemical Co., Inc.)

<Evaluation of Polyvalent Carboxylic Acid Condensate Properties 1>

The number-average molecular weight, viscosity, softening point and outer appearance of each of the polyvalent carboxylic acid condensates of Synthesis Examples A1, A2, A3, A4 A5 and A6 were evaluated. The results are shown in Table 1.

The number-average molecular weight Mn was measured by gel permeation chromatography (GPC) using a calibration curve based on standard polystyrene, under the following conditions.

Apparatus: Pump (Model L-6200, trade name of Hitachi, Ltd.), columns (TSKgel-G5000HXL and TSKgel-G2000HXL, trade names of Tosoh Corp.) and detector (Model L-3300RI, trade name of Hitachi, Ltd.).
Eluent: tetrahydrofuran, flow rate: 1.0 mL/min
Measuring temperature: 30° C.

The viscosity measurement was conducted using an ICI cone-plate Brookfield viscometer by Research Equipment (London) Ltd. Tables 2 and 3 show the 150° C. viscosity for each mixture of all of the curing agent components in the resin composition.

The softening point was measured by a ring and ball softening point test based on JIS K 2207. The outer appearance was judged visually.

curing time of 90 seconds, and was evaluated in the following manner. The evaluation results are shown in Tables 2a, 2b and 3.

(Photoreflectance Test)

The obtained thermosetting resin composition was transfer molded under the conditions described above and then post-cured at 150° C. for 2 hours to form a test piece with a thickness of 1.0 mm. A Model V-750 integrating sphere spectrophotometer (trade name of JASCO Corp. was used for measurement of the initial optical reflectance of the test piece at a wavelength of 400 nm. The photoreflectance was evaluated on the following scale.

A: Optical reflectance of 80% or greater at optical wavelength of 400 nm.
B: Optical reflectance of 70% or greater and less than 80% at optical wavelength of 400 nm.
C: Optical reflectance of less than 70% at optical wavelength of 400 nm.

(Transfer Moldability)
(Spiral Flow)

A spiral flow measuring die conforming to EMMI-1-66 was used for transfer molding of the thermosetting resin composition under the conditions described above and measurement of the flow distance (cm) during the molding.

(Burr Length)

The obtained thermosetting resin composition was cast into a burr-measuring die (see FIG. 7) using a pot, and then cured to mold the thermosetting resin composition. The die temperature during molding was 180° C., the molding pressure was 6.9 MPa, the resin casting time (transfer time) was 10 seconds, the curing temperature was 180° C. and the

TABLE 1

|  | Synthesis Example A1 | Synthesis Example A2 | Synthesis Example A3 | Synthesis Example A4 | Synthesis Example A5 | Synthesis Example A6 |
| --- | --- | --- | --- | --- | --- | --- |
| Number-average mol. wt. Mn | 508 | 608 | 306 | 1200 | 950 | 750 |
| Viscosity (ICI cone-plate, 150° C., mPa · s) | 500 | 310 | 110 | 260 | 140 | 390 |
| Softening point (° C.) | 50-55 | 45-50 | 45-50 | 30-40 | 30-40 | 50-60 |
| Transparency | Colorless transparent | Colorless transparent | Colorless transparent | Colorless transparent | Colorless transparent | Yellow-brown opaque |

The polyvalent carboxylic acid condensates obtained in the Synthesis Examples were very easily manageable in terms of both softening point and viscosity for production of thermosetting resin compositions, and they are suitable for use as curing agents in thermosetting resin compositions.

<Preparation of Thermosetting Resin Compositions>

Examples 1-23 Comparative Examples 1-3

After premixing the (A) epoxy resin and (B) curing agent in the mixing ratios (by weight) listed in Tables 2a, 2b and 3, the remaining components were added and a mixer was used for thorough mixing, and then the mixture was melt kneaded with a mixing roll under prescribed conditions and cooled and pulverized to prepare thermosetting resin compositions for Examples 1-23 and Comparative Examples 1-3.

<Evaluation of Thermosetting Resin Compositions>

Each of the obtained thermosetting resin compositions was used for transfer molding under conditions with a molding die temperature of 180° C., a molding pressure of 6.9 MPa and a curing time was 90 seconds. After molding, the cope of the burr-measuring die was removed and the maximum length of the burrs produced by flow between the cope and drag of the die during molding was measured using a caliper.

Figure 7:
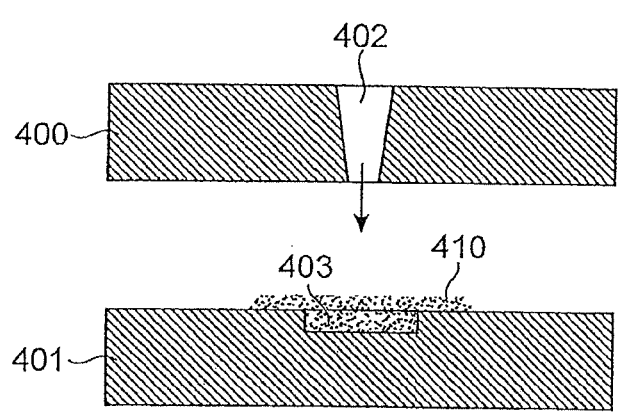
FIG. 7 is a schematic view showing the structure of the burr-measuring die used for measurement of burr length, and burrs.
Figure 7:
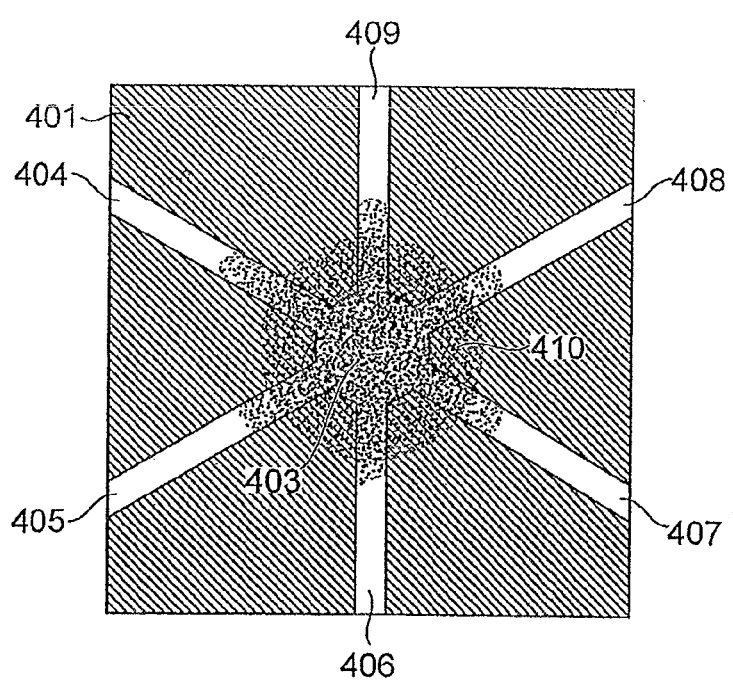

FIG. 7 is a schematic view showing the structure of the burr-measuring die used for measurement of burr length, and the burrs, where (a) is a side cross-sectional view and (b) is a plan view. As seen in FIG. 7, the burr-measuring die is constructed with a cope 400 and drag 401 pair, the cope 400 having a resin sprue 402. The drag 401 has a cavity 403 opposite the resin sprue 402, and 6 slits 404, 405, 406, 407, 408 and 409 extending from the cavity 403 to the outer periphery of the die. The burrs are the cast and hardened sections of the thermosetting resin composition (resin burrs) 410 from around the cavity 403 along each slit, as shown in FIG. 7. The "burr length" according to the invention is the value of the maximum length in the radial direction of the cured product (resin burrs 410) that has seeped out from the cavity 403 at the die center into the gaps between the cope 400 and drag 401 of the die, when the burr-measuring die shown in FIG. 7 is used for transfer molding, as measured with a caliper. For the burr-measuring die dimensions, the outer shapes of the cope 400 and drag 401 are (140 mm)×(140 mm), the resin sprue diameter is 7 mm at the top and 4 mm at the bottom, the cavity diameter is 30 mm, the cavity depth is 4 mm, and the depths of the six slits 404 to 409 are 75, 50, 30, 20, 10 and 2 μm, respectively.

TABLE 2a

|  |  | Example |  |  |  |  |  |  |  |  |  |  |  |  |  |
|---|---|---|---|---|---|---|---|---|---|---|---|---|---|---|---|
|  |  | 1 | 2 | 3 | 4 | 5 | 6 | 7 | 8 | 9 | 10 | 11 | 12 | 13 | 14 |
| Epoxy resin | Trisglycidyl isocyanurate (*1) | 100 | 100 | 100 | 100 | 100 | 100 | 100 | 100 | 100 | 100 | 100 | 100 | — | — |
|  | 3,4-Epoxycyclohexenylmethyl-3',4'-epoxycyclohexene carboxylate (*2) | — | — | — | — | — | — | — | — | — | — | — | — | 85 | 85 |
| Curing agent | Hexahydrophthalic anhydride (*3) | 99 | 99 | 62 | 62 | — | 111 | 99 | 62 | 99 | — | 120 | — | 108 | 68 |
|  | Hydrogenated trimellitic-1,2-anhydride (*4) | — | — | — | — | — | — | — | — | — | — | — | 90 | — | — |
|  | Synthesis Example A1 | 23 | 23 | 58 | 58 | 102 | — | — | — | — | — | — | — | 26 | 63 |
|  | Synthesis Example A2 | — | — | — | — | — | 12 | 23 | 58 | — | — | 5 | — | — | — |
|  | Synthesis Example A3 | — | — | — | — | — | — | — | — | 16 | 93 | — | — | — | — |
|  | ICI cone-plate viscosity of curing agent component (mPa·s) | 22 | 22 | 27 | 27 | 500 | 25 | 30 | 100 | 110 | 15 | 5 | 35 | 15 | 15 |
|  | (Equivalents to 1 epoxy group equivalent) | (0.8) | (0.8) | (0.8) | (0.8) | (0.8) | (0.8) | (0.8) | (0.8) | (0.8) | (0.8) | (0.8) | (0.8) | (0.8) | (0.8) |
| Curing accelerator | Tetra-n-butylphosphonium-o,o-diethyl phosphorodithioate (*5) | 2.2 | 2.2 | 2.2 | 2.2 | 2.2 | 2.2 | 2.2 | 2.2 | 2.2 | 2.2 | 2.2 | 2.2 | 2.2 | 2.2 |
| Coupling agent | Trimethoxyepoxysilane (*6) | 7.0 | 7.0 | 7.0 | 7.0 | 7.0 | 7.0 | 7.0 | 7.0 | 7.0 | 7.0 | 7.0 | 7.0 | 7.0 | 7.0 |
| Inorganic filler | Molten spherical silica (mean particle size: 6 μm) (*7) | 796 | 700 | 796 | 700 | 700 | 700 | 700 | 700 | 700 | 700 | 700 | 700 | 700 | 700 |
| White pigment | Hollow particles (mean particle size: 27 μm) (*8) | 217 | 194 | 217 | 194 | 194 | 194 | 194 | 194 | 194 | 194 | 194 | 194 | 194 | 194 |
|  | Alumina (mean particle size: 1 μm) (*9) | 705 | 630 | 705 | 630 | 630 | 630 | 630 | 630 | 630 | 630 | 630 | 630 | 630 | 630 |
| Properties | Initial optical reflectance (%) | A | A | A | A | A | A | A | A | A | A | A | A | A | A |
|  | Spiral flow (cm) | 120 | 150 | 89 | 95 | 70 | 132 | 120 | 80 | 130 | 78 | 140 | 30 | 220 | 180 |
|  | Burrs (mm) | 0.2 | 0.5 | 0.0 | 0.0 | 0.0 | 1.0 | 0.3 | 0.0 | 1.0 | 0.0 | 3.0 | 0.0 | 1.0 | 0.2 |

TABLE 2b

|  |  | Example |  |  |  |  |  |  |  |  |
|---|---|---|---|---|---|---|---|---|---|---|
|  |  | 15 | 16 | 17 | 18 | 19 | 20 | 21 | 22 | 23 |
| Epoxy resin | Trisglycidyl isocyanurate (*1) | 100 | 100 | 100 | 100 | 100 | 100 | 100 | 100 | 100 |
|  | 3,4-Epoxycyclohexenylmethyl-3',4'-epoxycyclohexene carboxylate (*2) | — | — | — | — | — | — | — | — | — |
| Curing agent | Hexahydrophthalic anhydride (*3) | 99 | 62 | — | 99 | 62 | — | 99 | 62 | — |
|  | Hydrogenated trimellitic-1,2-anhydride (*4) | — | — | — | — | — | — | — | — | — |
|  | Synthesis Example A4 | 23 | 58 | 102 | — | — | — | — | — | — |
|  | Synthesis Example A5 | — | — | — | 27 | 63 | 124 | — | — | — |
|  | Synthesis Example A6 | — | — | — | — | — | — | 24 | 60 | 105 |
|  | ICI cone-plate viscosity of curing agent component (mPa·s) | 10 | 14 | 300 | 15 | 32 | 430 | 30 | 43 | 650 |
|  | (Equivalents to 1 epoxy group equivalent) | (0.8) | (0.8) | (0.8) | (0.8) | (0.8) | (0.8) | (0.8) | (0.8) | (0.8) |
| Curing accelerator | Tetra-n-butylphosphonium-o,o-diethyl phosphorodithioate (*5) | 2.2 | 2.2 | 2.2 | 2.2 | 2.2 | 2.2 | 2.2 | 2.2 | 2.2 |
| Coupling agent | Trimethoxyepoxysilane (*6) | 7.0 | 7.0 | 7.0 | 7.0 | 7.0 | 7.0 | 7.0 | 7.0 | 7.0 |
| Inorganic filler | Molten spherical silica (mean particle size: 6 μm) (*7) | 700 | 700 | 700 | 700 | 700 | 700 | 700 | 700 | 700 |
| White pigment | Hollow particles (mean particle size: 27 μm) (*8) | 194 | 194 | 194 | 194 | 194 | 194 | 194 | 194 | 194 |
|  | Alumina (mean particle size: 1 μm) (*9) | 630 | 630 | 630 | 630 | 630 | 630 | 630 | 630 | 630 |
| Properties | Initial optical reflectance (%) | A | A | A | A | A | A | A | A | A |
|  | Spiral flow (cm) | 165 | 103 | 85 | 155 | 126 | 97 | 142 | 120 | 90 |
|  | Burrs (mm) | 0.5 | 0.2 | 0.0 | 0.5 | 0.2 | 0.0 | 0.5 | 0.2 | 0.0 |

TABLE 3

|  |  | Comp. Ex. | | |
| --- | --- | --- | --- | --- |
|  |  | 1 | 2 | 3 |
| Epoxy resin | Trisglycidyl isocyanurate (*1) | 100 | 100 | — |
|  | 3,4-Epoxycyclohexenylmethyl-3',4'-epoxycyclohexene carboxylate (*2) | — | — | 90 |
| Curing agent | Hexahydrophthalic anhydride (*3) | 123 | 139 | 137 |
|  | Hydrogenated trimellitic-1,2-anhydride (*4) | — | — | — |
|  | Synthesis Example A1 | — | — | — |
|  | Synthesis Example A2 | — | — | — |
|  | Synthesis Example A3 | — | — | — |
|  | ICI cone-plate viscosity of curing agent component (mPa·s) | <1 | <1 | <1 |
|  | (Equivalents to 1 epoxy group equivalent) | (0.8) | (0.9) | (0.9) |
| Curing accelerator | Tetra-n-butylphosphonium-o,o-diethyl phosphorodithioate (*5) | 2.2 | 2.2 | 2.2 |
| Coupling agent | Trimethoxyepoxysilane (*6) | 7.0 | 7.0 | 7.0 |
| Inorganic filler | Molten spherical silica (mean particle size: 6 μm) (*7) | 700 | 796 | 700 |
| White pigment | Hollow particles (mean particle size: 27 μm) (*8) | 194 | 217 | 194 |
|  | Alumina (mean particle size: 1 μm) (*9) | 630 | 705 | 630 |
| Properties | Initial optical reflectance (%) | A | A | A |
|  | Spiral flow (cm) | 150 | 175 | 200 |
|  | Burrs (mm) | 6.0 | 9.0 | 16.0 |

Footnotes *1-*9 in Tables 2a, 2b and 3 are as follows.
(*1): Trisglycidyl isocyanurate (100 epoxy equivalents, trade name: TEPIC-S by Nissan Chemical Industries, Ltd.)
(*2): 3,4-Epoxycyclohexenylmethyl-3',4'-epoxycyclohexene carboxylate (trade name: CELLOXIDE 2021P by Dicel Chemical Industries, Ltd.)
(*3): Hexahydrophthalic anhydride (Wako Pure Chemical Industries, Ltd.)
(*4): Hydrogenated 1,2-trimellitic anhydride (Mitsubishi Gas Chemical Co., Inc.)
(*5): Tetra-n-butylphosphonium-o,o-diethyl phosphorodithioate (trade name: PX-4ET by Nippon Chemical Industrial Co., Ltd.)
(*6): Trimethoxyepoxysilane (trade name: A-187 by Dow Corning Toray Co., Ltd.)
(*7): Molten silica (trade name: FB-301 by Denki Kagaku Kogyo Co., Ltd.)
(*8): Hollow particles (trade name: S60-HS by Sumitomo-3M)
(*9): Alumina (trade name: AO-25R by Admatechs)

As shown in Tables 2a, 2b, the thermosetting resin compositions of the invention have excellent photoreflectance and are able to adequately reduce burrs, i.e. resin smudge.

Using a thermosetting resin composition of the invention for transfer molding can yield a photosemiconductor element mounting board having a photosemiconductor element mounting region with adequately reduced resin smudge. This allows a photosemiconductor element to be mounted in the opening of the photosemiconductor element mounting region and electrical connection to be established between the photosemiconductor element and metal wiring by a known method such as a bonding wire. The invention also eliminates the need for a step of burr removal in the production process for a photosemiconductor element mounting board, and is thus highly advantageous in terms of productivity including cost and production time.

<Preparation of Polyvalent Carboxylic Acid Condensate 2>

Each of the repeating unit monomers and end monomers indicated in Examples A1, A2, A3, A4 and A5 and Comparative Example A1 were circulated in acetic anhydride for 5-30 minutes under a nitrogen atmosphere. The liquid temperature was then raised to 180° C., and the acetic acid and water produced by reaction in an open system under a nitrogen stream were removed. When no further production of volatilizing components was detected, the pressure inside the reactor was reduced while conducting melt condensation at 150° C. for 3 hours to obtain a polyvalent carboxylic acid condensate.

Example A1

Repeating unit: 125 g of hydrogenated terephthalic acid (product of Tokyo Chemical Industry Co., Ltd.)
Ends: 126 g of hydrogenated trimellitic anhydride (product of Mitsubishi Gas Chemical Co., Inc.)

Example A2

Repeating unit: 218 g of hydrogenated terephthalic acid (product of Tokyo Chemical Industry Co., Ltd.)
Ends: 86 g of hydrogenated trimellitic anhydride (product of Mitsubishi Gas Chemical Co., Inc.)

Example A3

Repeating unit: None
Ends: 100 g of hydrogenated 1,2-trimellitic anhydride (product of Mitsubishi Gas Chemical Co., Inc.)

Example A4

Repeating unit: 125 g of hydrogenated isophthalic acid (product of Iwatani Gas Chemical Industry Co., Ltd.)
Ends: 126 g of hydrogenated 1,2-trimellitic anhydride (product of Mitsubishi Gas Chemical Co., Inc.)

Example A5

Repeating unit: 226 g of hydrogenated naphtalene-1,10-dicarboxylic acid derived from hydrogenated naphtalene-1, 10-dicarboxylic acid dimethyl ester (product of Iwatani Gas Chemical Industry Co., Ltd.)

Ends: 174 g of hydrogenated 1,2-trimellitic anhydride (product of Mitsubishi Gas Chemical Co., Inc.)

Comparative Example A1

Repeating unit: 166 g of terephthalic acid (product of Wako Pure Chemical Industries, Ltd.)

Ends: 168 g of trimellitic anhydride (product of Wako Pure Chemical Industries, Ltd.)

<Evaluation of Polyvalent Carboxylic Acid Condensate Properties 2>

The number-average molecular weight, viscosity, softening point, infrared absorption spectrum, ultraviolet-visible absorption spectrum and outer appearance of each of the polyvalent carboxylic acid condensates of Examples A1, A2, A3, A4 and A5 and Comparative Example A1 were evaluated. The results of the evaluation are shown in Table 4.

The number-average molecular weight Mn was measured with the same conditions as above. However, the polyvalent carboxylic acid condensate of Comparative Example A1 was insoluble in the solvent and therefore the Mn could not be measured.

Figure 9:
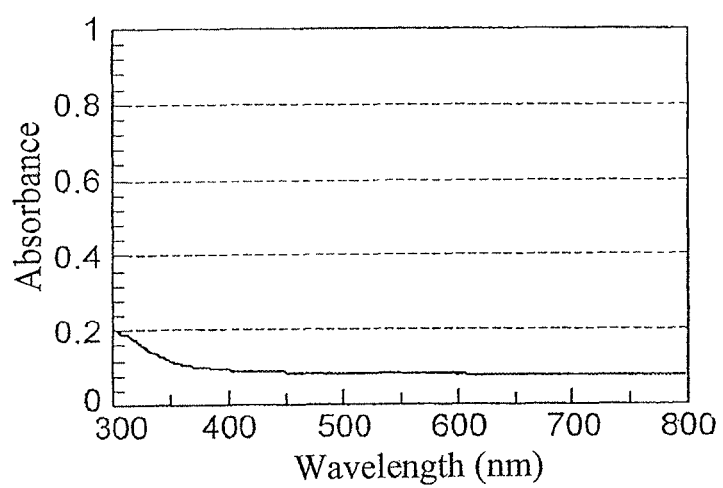
FIG. 9 is an ultraviolet-visible absorption spectrum of the polyvalent carboxylic acid condensate of Example A1.

The viscosity measurement was conducted using an ICI cone-plate Brookfield viscometer by Research Equipment (London) Ltd. The softening point and outer appearance were evaluated by heating the obtained compound on a hot plate and visually confirming changes in the state.

a Model V-750 spectrophotometer (product of JASCO Corp.). The obtained ultraviolet-visible absorption spectrum is shown in FIG. 9.

Examples B1-B9, Comparative Examples B1-B2

(Curability of Epoxy Resin Compositions)

The polyvalent carboxylic acid condensates of Examples A1, A3, A4, A5 and Comparative Example A1, hexahydrophthalic anhydride and methylhexahydrophthalic anhydride were combined in the mixing ratios listed in Table 5, and each mixture was melted at 120° C. and stirred until the materials were completely miscible, to obtain acid anhydride-based curing agents. Each of the curing agents was mixed with an epoxy resin (triglycidyl isocyanurate) and heated to 120° C. and stirred in a molten state until the materials were completely miscible. The epoxy resin was mixed with the curing agent in an amount for the proportion listed in Table 5 with respect to each component in the curing agent. Heating was then interrupted, and when the temperature of the mixture fell below 80° C., a curing catalyst (tetra-n-butylphosphonium-o,o-diethyl phosphorodithioate) was added and the mixture was vigorously stirred to obtain a translucent epoxy resin composition. The units for the amounts of each component in Table 5 are in parts by weight, and "–" indicates that the material was not added. The resin compositions of Examples B1-B9 and Comparative Examples B1 and B2 prepared in the manner described above were evaluated by the following property tests. The evaluation results are shown in Table 5.

TABLE 4

|  | Example A1 | Example A2 | Example A3 | Example A4 | Example A5 | Comp. Ex. A1 |
|---|---|---|---|---|---|---|
| Number-average mol. wt. Mn | 508 | 608 | 306 | 1200 | 950 | Insoluble in solvent |
| Viscosity (ICI cone-plate, 150° C., mPa · s) | 500 | 310 | 110 | 260 | 140 | Solid |
| Softening point (° C.) | 50-55 | 45-50 | 45-50 | 30-40 | 30-40 | 170 (incomplete dissolution) |
| Description | Solid | Solid | Solid | Solid | Solid | Solid |
| Transparency | Colorless transparent | Colorless transparent | Colorless transparent | Colorless transparent | Colorless transparent | Brown |

Infrared Absorption (FT-IR) Spectrum

Figure 8:
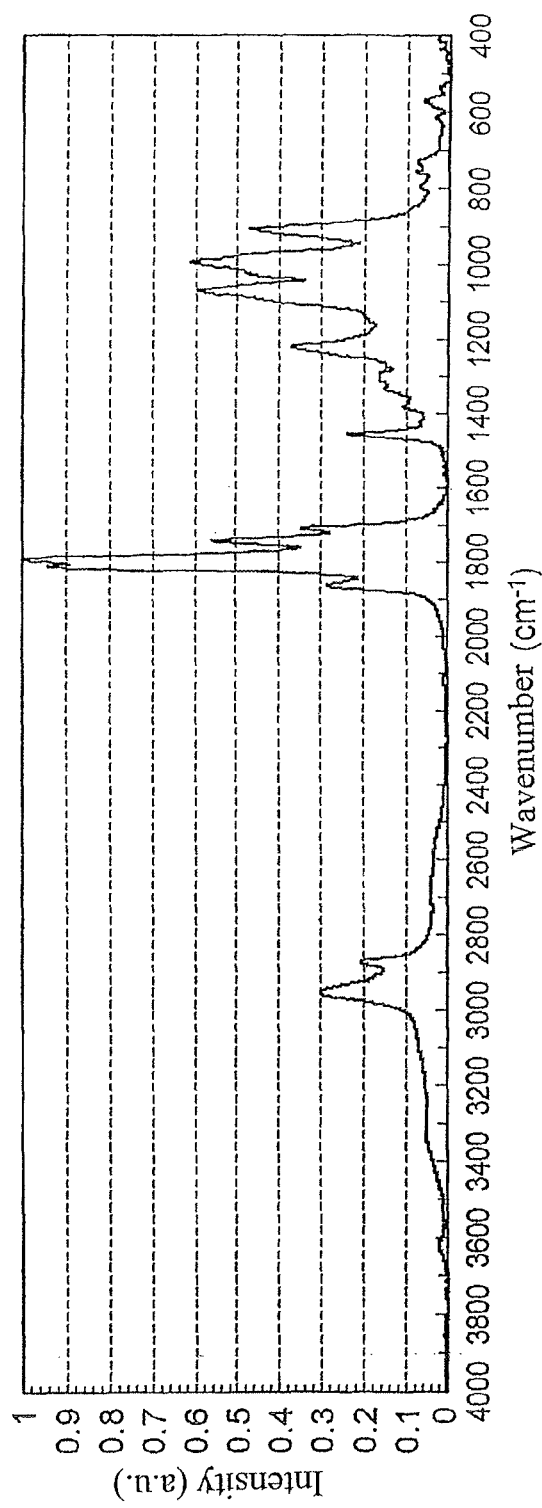
FIG. 8 is an FT-IR spectrum of the polyvalent carboxylic acid condensate of Example A1.

A tetrahydrofuran solution of the polyvalent carboxylic acid condensate of Example A1 was cast onto a KRs crystal board to form a sample cell, and the infrared absorption spectrum at a wavenumber of 4000-400 cm$^{-1}$ was measured using an FTS300 MX spectrophotometer by Biorad. The obtained infrared absorption spectrum is shown in FIG. 8.

Ultraviolet-Visible Absorption Spectrum

The polyvalent carboxylic acid condensate of Example A1 was worked to form a laminar test piece with a thickness of 1.0 mm. The ultraviolet-visible absorption spectrum of the test piece at a wavelength of 300-800 nm was measured using (Compatibility, Transparency and Color)

The resin compositions and their cured products were visually examined and their compatibility, transparency and color were evaluated. The cured product color was evaluated after curing (initial) and after standing at 150° C. for 4 hours.

(Optical Transparency Test)

Each resin composition was heated at 100° C. for 4 hours, and then post-cured at 150° C. for 2 hours to prepare a cured composition with a thickness of 1.0 mm as a test piece. The light transmittance of the test piece at a wavelength of 460 nm was measured using a Model V-750 spectrophotometer (product of JASCO Corp.).

TABLE 5

|  |  | Example |  |  |  |  |  |  |  |  | Comp. Ex. |  |
|---|---|---|---|---|---|---|---|---|---|---|---|---|
|  |  | B1 | B2 | B3 | B4 | B5 | B6 | B7 | B8 | B9 | B1 | B2 |
| Curing agent | Example A1 | 55 | 55 | 137 | 70 | 175 | 205 | — | — | — | — | — |
|  | Example A3 | — | — | — | — | — | — | 126 | — | — | — | — |
|  | Example A4 | — | — | — | — | — | — | — | 137 | — | — | — |
|  | Example A5 | — | — | — | — | — | — | — | — | 162 | — | — |
|  | Comp. Ex. A1 | — | — | — | — | — | — | — | — | — | 66 | 66 |
|  | Hexahydrophthalic anhydride (*4) | 62 | — | — | 80 | — | — | — | — | — | 62 | — |
|  | Methylhexahydrophthalic anhydride (*5) | — | 84 | — | — | — | — | — | — | — | — | 84 |
| Epoxy resin | Triglycidyl isocyanurate (*1) | 100 | 100 | 100 | — | — | — | — | — | — | 100 | 100 |
|  | 3,4-Epoxycyclohexenylmethyl-3',4'-epoxycyclohexene carboxylate (*2) | — | — | — | 100 | 100 | — | 100 | 100 | 100 | — | — |
|  | Diglycidylester hexahydrophthalate (*3) | — | — | — | — | — | 100 | — | — | — | — | — |
| Curing catalyst | Tetra-n-butylphosphonium-o,o-diethyl phosphorodithioate (*6) | 1.0 | 1.0 | 1.0 | 1.0 | 1.0 | 1.0 | 1.0 | 1.0 | 1.0 | 1.0 | 1.0 |
| 120° C. compatibility between curing agents |  | Compatible | Compatible | Compatible | Compatible | Compatible | Compatible | Compatible | Compatible | Compatible | Incompatible | Incompatible |
| 120° C. compatibility between epoxy resin and curing agent |  | Compatible | Compatible | Compatible | Compatible | Compatible | Compatible | Compatible | Compatible | Compatible | Incompatible | Incompatible |
| Properties of cured product | Transparency | Transparent | Transparent | Transparent | Transparent | Transparent | Transparent | Transparent | Transparent | Transparent | No homogeneous curing | No homogeneous curing |
|  | Optical transmittance at 460 nm wavelength (%) | 93 | 90 | 91 | 89 | 89 | 87 | 88 | 89 | 89 |  |  |
|  | Cured color | Colorless | Colorless | Colorless | Colorless | Colorless | Colorless | Colorless | Colorless | Colorless |  |  |
|  | Color after standing at 150° C. for 4 hrs | Colorless | Colorless | Colorless | Colorless | Colorless | Colorless | Colorless | Colorless | Colorless |  |  |

The footnotes (*1-6) in Table 5 are as follows.
(*1): Trisglycidyl isocyanurate (100 epoxy equivalents, trade name: TEPIC-S by Nissan Chemical Industries, Ltd.)
(*2): 3,4-Epoxycyclohexenylmethyl-3',4'-epoxycyclohexene carboxylate (trade name: CELLOXIDE 2021P by Dicel Chemical Industries, Ltd.)
(*3): Diglycidyl hexahydrophthalate ester (trade name: SR-HHPA by Sakamoto Yakuhin Kogyo Co., Ltd.)
(*4): Hexahydrophthalic anhydride (Wako Pure Chemical Industries, Ltd.)
(*5): Methylhexahydrophthalic anhydride (Hitachi Chemical Co., Ltd.)
(*6): Tetra-n-butylphosphonium-o,o-diethyl phosphorodithioate (trade name: PX-4ET by Nippon Chemical Industrial Co., Ltd.)

Examples C1-C9

Polyvalent carboxylic acid condensate-containing epoxy resin compositions were used as application examples for production of transfer molding resin compositions and evaluation of the same.

<Production of Transfer Molding Resin Compositions>

The polyvalent carboxylic acid condensates of Examples A1, A2, A3, A4 and A5 and the other components were combined in the mixing ratios listed in Table 6. The mixture was thoroughly mixed with a mixer, melt kneaded with a mixing roll under prescribed conditions and cooled, and then pulverized, to obtain transfer molding resin compositions for Examples C1-C9. The units for the component amounts in Table 6 are parts by weight. Blank cells indicate that no component was added.

(Transfer Moldability)

Each of the obtained transfer molding resin compositions was used for transfer molding under conditions with a molding die temperature of 180° C., a molding pressure of 6.9 MPa and a curing time of 90 seconds, and was evaluated in the following manner. The evaluation results are shown in Table 6.

1) Spiral Flow

A spiral flow measuring die conforming to EMMI-1-66 was used for transfer molding of the resin composition under the conditions described above and measurement of the flow distance (cm) during the molding.

2) Hot Hardness

The resin composition was transfer molded into a discoid form with 50 mm diameter×3 mm thickness under the molding conditions described above, and immediately after molding, a Model D Shore hardness meter was used to measure the hardness of the compact.

3) Gel Time

Using 3 g of the resin composition as a measuring sample, the torque curve at 180° C. was measured with a CURELASTOMETER by JSR and the time to rising was recorded as the gel time (sec).

TABLE 6

|  |  | Example C |  |  |  |  |  |  |  |  |
|---|---|---|---|---|---|---|---|---|---|---|
|  |  | 1 | 2 | 3 | 4 | 5 | 6 | 7 | 8 | 9 |
| Mixture components | Trisglycidyl isocyanurate (*1) | 100 | 100 | 100 | 100 | 100 | 100 | 100 | 100 | 100 |
|  | Hexahydrophthalic anhydride (*2) | 99 | 62 | 62 | 111 | 99 | 62 | 62 | 62 | 62 |
|  | Example A1 | 23 | 58 | 58 |  |  |  |  |  |  |

TABLE 6-continued

| | | Example C | | | | | | | | |
|---|---|---|---|---|---|---|---|---|---|---|
| | | 1 | 2 | 3 | 4 | 5 | 6 | 7 | 8 | 9 |
| | Example A2 | | | | 12 | 23 | 58 | | | |
| | Example A3 | | | | | | | 54 | | |
| | Example A4 | | | | | | | | 58 | |
| | Example A5 | | | | | | | | | 70 |
| | Tetra-n-butylphosphonium-o,o-diethyl phosphorodithioate (*4) | 2.2 | 2.2 | 2.2 | 2.2 | 2.2 | 2.2 | 2.2 | 2.2 | 2.2 |
| | Trimethoxyepoxysilane (*5) | 7.0 | 7.0 | 7.0 | 7.0 | 7.0 | 7.0 | 7.0 | 7.0 | 7.0 |
| | Molten spherical silica (center particle size: 6 μm) (*6) | 796 | 796 | 700 | 796 | 796 | 739 | 739 | 739 | 739 |
| | Hollow particles (center particle size: 27 μm) (*7) | 217 | 217 | 194 | 217 | 217 | 201 | 201 | 201 | 201 |
| | Alumina (center particle size: 1 μm) (*8) | 705 | 705 | 630 | 705 | 705 | 645 | 645 | 645 | 645 |
| Properties | Spiral flow (cm) | 120 | 89 | 95 | 132 | 120 | 80 | 100 | 90 | 75 |
| | Hot hardness | 89 | 90 | 90 | 89 | 90 | 90 | 90 | 90 | 90 |
| | Gel time (sec) | 24 | 19 | 15 | 21 | 18 | 16 | 16 | 16 | 16 |

The footnotes (*1, 2) and (4-8) in Table 6 are as follows.
(*1): Trisglycidyl isocyanurate (trade name: TEPIC-S by Nissan Chemical Industries, Ltd.)
(*2): Hexahydrophthalic anhydride (Wako Pure Chemical Industries, Ltd.)
(*4): Tetra-n-butylphosphonium-o,o-diethyl phosphorodithioate (trade name: PX-4ET by Nippon Chemical Industrial Co., Ltd.)
(*5): Trimethoxyepoxysilane (trade name: A-187 by Dow Corning Toray Co., Ltd.).
(*6): Molten silica (trade name: FB-301 by Denki Kagaku Kogyo Co., Ltd.)
(*7): Hollow particles (trade name: S60-HS by Sumitomo-3M)
(*8): Alumina (trade name: AO-802 by Admatechs)

As seen in Table 6, by heating hydrogenated terephthalic acid, which is a cyclohexane with a carboxylic acid at the 1,4-position, and hydrogenated trimellitic anhydride for reaction while removing acetic acid, it was possible to obtain a colorless transparent solid polyvalent carboxylic acid condensate (acid anhydride). However, it was not possible to obtain a colorless transparent polyvalent carboxylic acid condensate in Comparative Example A1 wherein a total aromatic polyvalent carboxylic acid condensate was produced.

As shown in FIG. 8, in each of the infrared absorption spectra (FT-IR) of the polyvalent carboxylic acid condensates synthesized in the examples there was detected a peak for an absorption signal derived from intermolecular condensed acid anhydrides. Also as shown in FIG. 9, the polyvalent carboxylic acid condensates synthesized in the examples had low absorption in the visible light region because they were composed of alicyclic skeletons containing no aromatic rings.

As seen in Table 5, the polyvalent carboxylic acid condensates of Examples A1, A3, A4 and A5 exhibited satisfactory compatibility with other acid anhydrides such as hexahydrophthalic anhydride and methylhexahydrophthalic anhydride, and could therefore be combined with other acid anhydrides to prepare an acid anhydride-based epoxy resin curing agent. Furthermore, since the obtained acid anhydride-based epoxy resin curing agent had good compatibility with polyfunctional epoxy resins such, as triglycidyl isocyanurate, it was possible to prepare a translucent epoxy resin composition. Moreover, the translucent cured product obtained by thermal curing reaction of the epoxy resin composition exhibited no coloration even when allowed to stand in a high-temperature environment of 150° C., and therefore the cured product had excellent translucency and heat resistance. On the other hand, the total aromatic polyvalent carboxylic acid condensate of Comparative Example A1 had low compatibility with other acid anhydrides, and molten mixtures thereof with other acid anhydrides were opaque. Epoxy resin compositions obtained by combination thereof with epoxy resins could not form homogeneous cured products when subjected to thermosetting reaction.

Resin compositions containing the polyvalent carboxylic acid condensates of Examples A1, A2, A3, A4 and A5 as curing agent components had transfer moldability equivalent to that of common semiconductor sealing resin compositions.

<Preparation of Thermosetting Resin Compositions>

Examples D1 and D2

After premixing the epoxy resin and curing agent in the mixing ratios (by parts by weight) listed in Table 7, the remaining components were added and a mixer was used for thorough mixing, and then the mixture was melt kneaded with a mixing roll under prescribed conditions and cooled and pulverized to prepare thermosetting resin compositions for Examples D1 and D2.

<Evaluation of Thermosetting Resin Compositions>

Each of the obtained thermosetting resin compositions was used for transfer molding with an "ATOM-FX" transfer molding machine by MTEX, under conditions with a molding die temperature of 180° C., a molding pressure of 6.9 MPa and a curing time of 90 seconds, and was evaluated in the following manner. The evaluation results are shown in Table 7.

(Alkali Resistance Evaluation of Cured Products)

A 10 mm×10 mm×3 mm test piece prepared under the molding conditions described above was weighed before and after dipping in a sodium hydroxide aqueous solution, and the degree of elution of the cured product with respect to the aqueous alkali solution was evaluated. The dipping conditions were a sodium hydroxide aqueous solution concentration of 125 g/L, a dipping temperature of 50° C., and a dipping time of 5 minutes or 30 minutes. The dipped test piece was rinsed with water after dipping and subjected to ultrasonic treatment in water for a period of 30 seconds, re-rinsed with water, and then dried at 150° C. for 30 minutes, after which the change in weight was measured.

Weight change(%)=(weight of test piece before dipping(g)−weight of test piece after dipping(g))/weight of test piece before dipping(g)×100

(Evaluation of Deflush Property of Photosemiconductor Element Mounting Boards)

<Fabrication of Photosemiconductor Element Mounting Boards>

Each of the obtained thermosetting resin compositions was used for molding with an "ATOM-FX" transfer molding machine by MTEX, under conditions with a molding die temperature of 180° C., a clamp pressure of 20 t, an injection pressure of 7 MPa and a molding time of 90 seconds, to fabricate a photosemiconductor element mounting board.

As lead frames there were used test lead frames allowing formation of 12 photosemiconductor element mounting boards with an opening outer periphery of 10 mm×10 mm for each lead frame (2 rows×6 columns). The metal wiring to serve as the photosemiconductor element mounting region on the lead frame was designed as a pattern having 3 pairs each of cathodes and anodes in each photosemiconductor element mounting region, using a copper lead frame with a thickness of 0.25 μm, surface-plated with Ag.

(Evaluation of Resin Smudge Removal)

The photosemiconductor device-mounting board used for this test had resin smudge on the lead frame when the board was molded with a single-side mold.

The photosemiconductor element mounting board having resin smudge on the lead frame was used for electrolytic degreasing with an aqueous alkali solution, and after rinsing the board while applying ultrasonic waves for 30 seconds, the resin smudge (burr formation) was removed by air blowing. The presence or absence of residual resin smudge after deflushing, and the outer appearance of the reflector section (surface roughness and degree of elution) were evaluated based on the following.

A: Virtually no change in outer appearance.

B: Irregularities due to elution of resin components from the cured product.

TABLE 7

|  |  | Example D1 | Example D2 |
|---|---|---|---|
| Epoxy resin | Trisglycidyl isocyanurate (*1) | 20.0 | 20.0 |
| Curing agent | Synthesis Example 6 | 3.6 | — |
|  | Synthesis Example 1 | — | 3.6 |
|  | Succinic anhydride (*2) | 7.2 | 7.2 |
|  | Hexahydrophthalic anhydride (*3) | 6.5 | 6.4 |
| Curing accelerator | Tetra-n-butylphosphonium (*4) tetraphenolborate | 0.7 | 0.5 |
| Coupling agent | Trimethoxyepoxysilane (*5) | 0.4 | 0.4 |
| Inorganic filter | FB-950 (*6) | 62 | 62 |
|  | SO-25R (*7) | 16 | 15 |
| White pigment | S60-HS (*8) | 21 | 21 |
|  | CR-63 (*9) | 74 | 74 |
| Alkali resistance | Weight reduction after 5 min dipping treatment (%) | 0.6 | 1.1 |
|  | Weight reduction after 30 min dipping treatment (%) | 2.3 | 5.43 |

TABLE 7-continued

|  |  | Example D1 | Example D2 |
|---|---|---|---|
| Outer appearance | Residual burrs | None | None |
|  | Surface roughness | A | B |

The footnotes *1-9 in Table 7 are as follows.
(*1): Trisglycidyl isocyanurate (100 epoxy equivalents, trade name: TEPIC-S by Nissan Chemical Industries, Ltd.)
(*2): Succinic anhydride (trade name: LICASID by New Japan Chemical Co., Ltd.)
(*3): Hexahydrophthalic anhydride (trade name: LICASID HH by New Japan Chemical Co., Ltd.)
(*4): Tetra-n-butylphosphonium-o,o-diethylphosphorodithioate (trade name: PX-4ET by Nippon Chemical Industrial Co., Ltd.)
(*5): Trimethoxyepoxysilane (trade name: S6040 by Dow Corning Toray Co., Ltd.).
(*6): Molten silica (trade name: FB-950 by Denki Kagaku Kogyo Co., Ltd.)
(*7): Molten silica (trade name: S0-25R by Denki Kagaku Kogyo Co., Ltd.)
(*8): Hollow particles (trade name: S60-HS by Sumitomo-3M)
(*9): Titanium oxide (trade name: CR-63 by Ishihara Sangyo Kaisha, Ltd.)

As shown in Table 7, the thermosetting resin compositions of the invention had increased alkali resistance of the cured products, and the surface roughness after electrolytic degreasing of the transfer molded boards was improved, by using an aromatic trimellitic anhydride as the terminal structure, when a polyvalent carboxylic acid condensate was used as the curing agent.

Industrial Applicability

According to the invention it is possible to provide a thermosetting resin composition and epoxy resin molding material with reduced resin smudge during molding and sufficiently excellent moldability, as well as a photosemiconductor element mounting board and method for producing it, and a photosemiconductor device, which employ the same. Also, when used as a curing agent for thermosetting resins such as epoxy resins, the polyvalent carboxylic acid condensate of the invention can yield transparent cured products with low coloration.

The invention claimed is:

1. A polyvalent carboxylic acid condensate comprising a component represented by the following formula (X):

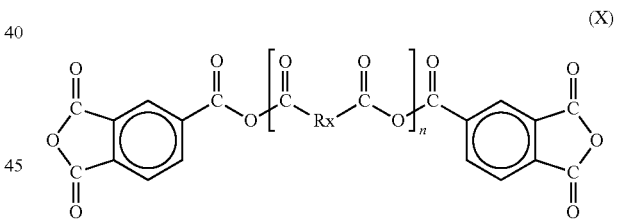

(In formula (X), $R_x$ represents a divalent group with an aliphatic hydrocarbon ring, wherein the aliphatic hydrocarbon ring is optionally substituted with a halogen atom or a straight-chain or branched hydrocarbon group, multiple $R_x$ groups in the same molecule can be the same or different, and n represents an integer of 1 or greater.)

2. A polyvalent carboxylic acid condensate according to claim 1, wherein $R_x$ represents a divalent organic group derived from hydrogenated terephthalic acid.

* * * * *